US007053282B1

(12) United States Patent
Jung et al.

(10) Patent No.: US 7,053,282 B1
(45) Date of Patent: *May 30, 2006

(54) ALTERATION OF AMINO ACID COMPOSITIONS IN SEEDS

(75) Inventors: Rudolf Jung, Des Moines, IA (US); Larry R. Beach, Des Moines, IA (US); Virginia M. Dress, Clive, IA (US); A. Gururaj Rao, Urbandale, IA (US); Jerome P. Ranch, Dallas County, IA (US); David S. Ertl, Waukee, IA (US); Regina K. Higgins, Des Moines, IA (US)

(73) Assignee: Pioneer Hi-Bred International, Inc., Johnston, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 12 days.

(21) Appl. No.: 09/020,716

(22) Filed: Feb. 9, 1998

(51) Int. Cl.
*A01H 5/00* (2006.01)
*C12N 15/82* (2006.01)

(52) U.S. Cl. ............... 800/320; 800/287; 800/298; 435/419; 435/320.1

(58) Field of Classification Search ........... 435/419, 435/320.1, 69.1, 468, 440; 536/23.6; 800/278, 800/287, 298, 320
See application file for complete search history.

(56) References Cited

U.S. PATENT DOCUMENTS

| | | | | |
|---|---|---|---|---|
| 5,508,468 | A | 4/1996 | Lundquist et al. | 800/205 |
| 5,677,474 | A | 10/1997 | Rogers | 800/205 |
| 5,773,691 | A * | 6/1998 | Falco et al. | 800/205 |
| 5,811,654 | A | 9/1998 | Jaynes et al. | 800/205 |
| 5,885,801 | A | 3/1999 | Rao | 435/69.1 |
| 5,885,802 | A * | 3/1999 | Rao et al. | 435/69.1 |
| 5,990,389 | A | 11/1999 | Rao et al. | 800/250 |
| 6,160,208 | A | 12/2000 | Lundquist et al. | 800/320.1 |

FOREIGN PATENT DOCUMENTS

| | | |
|---|---|---|
| WO | WO 91/10725 | 7/1991 |
| WO | WO 93/03160 | 2/1993 |
| WO | WO 93/08682 | 5/1993 |
| WO | WO 94/16078 | 7/1994 |
| WO | WO 95/06128 | 3/1995 |
| WO | WO 96/38562 | 12/1996 |
| WO | WO 96/38563 | 12/1996 |
| WO | WO 96/38574 | 12/1996 |
| WO | WO 97/26366 | 7/1997 |
| WO | WO 97/28247 | 8/1997 |
| WO | WO 97/35023 | 9/1997 |
| WO | WO 97/41239 | 11/1997 |
| WO | WO 98/02563 | 1/1998 |
| WO | WO 98/26064 | 6/1998 |
| WO | WO 99/04024 | 1/1999 |
| WO | WO 99/16890 | 4/1999 |

OTHER PUBLICATIONS

Stam M, et al. "The silence of genes in transgenic plants." Ann. Bot. 79: 3-12, 1997.*
Koziel MG, et al. "Optimizing expression of transgenes with an emphasis on post-transcriptional events." Plant Mol. Biol. 32: 393-405, 1996.*
Smith CJS, et al. "Antisense RNA inhibition of polygalacturonase gene expression in transgenic tomatoes." Nature 334: 724-726, Aug. 25, 1988.*
Schernthaner JP, et al. "Endosperm-specific activity of a zein gene promoter in transgenic tobacco plants." EMBO 7: 1249-1255, 1988.*
Higgins et al., "Gene Structure, Protein Structure, and Regulation of the Synthesis of Sulfur-rich Protein in Pea Seeds", *J. Biol. Chem.*, vol. 261, No. 24, pp. 11124-11130 (1986).
Kirihara et al., "Isolation and sequence of a gene encoding a methionine-rich 10-kDa zein protein from maize", *Gene*, vol. 71, pp. 359-370 (1988).
Lilley, et al., "Isolation and Primary Structure for a Novel, Methionine-rich Protein from Sunflowerseeds (*Helianthus annus.* L)", Proceedings of the World Congress on Vegetable Protein Utilization in Human Foods and Animal Feedstuffs; Applewhite, T.H. (ed.), American Oil Chemists Soc., Champaign, IL, pp. 497-502 (1989).
Mak et al., "The amino acid sequence of wheat beta-purothionin", *Can J. Biochem*, 54(10):835-842 (1976).
Masumura et al., "cDNA cloning of an mRNA encoding a sulfur-rich 10kDa prolamin polypeptide in rice seeds", *Plant Molecular Biology*, 12:123-130 (1989).
Pedersen et al., "Sequence Analysis and Characterization of a Maize Gene Encoding a High-sulfur Zein Protein of $M_r$ 15,000", *J. Biol. Chem.*, vol. 261, No. 14, pp. 6279-6284 (1986).
Torrent et al., "Lysine-rich modified γ-zeins accumulate in protein bodies of transiently transformed maize endosperms", *Plant Molecular Biology* 34:139-149 (1997).

* cited by examiner

*Primary Examiner*—Elizabeth F. McElwain
(74) *Attorney, Agent, or Firm*—Kathryn K. Lappegard; Pioneer Hi-Bred International, Inc.

(57) ABSTRACT

The present invention provides a plant seed the endosperm of which is characterized as having an elevated level of a preselected amino acid. The present invention also provides expression cassettes, vectors, plants, plant cells and a method for enhancing the nutritional value of seeds.

9 Claims, No Drawings

SEQUENCE LISTING

<160> NUMBER OF SEQ ID NOS: 22

<210> SEQ ID NO 1
<211> LENGTH: 3363
<212> TYPE: DNA
<213> ORGANISM: Artificial Sequence
<220> FEATURE:
<223> OTHER INFORMATION: pBSKP vector with native alpha hordothionin
      sequence from Hordeum vulgare located from
      nucleotide 3361 to nucleotide 2947.

<400> SEQUENCE: 1

| | | | | | | |
|---|---|---|---|---|---|---|
| tcgacctcga | gggggggccc | ggtacccagc | ttttgttccc | tttagtgagg | gttaattgcg | 60 |
| cgcttggcgt | aatcatggtc | atagctgttt | cctgtgtgaa | attgttatcc | gctcacaatt | 120 |
| ccacacaaca | tacgagccgg | aagcataaag | tgtaaagcct | ggggtgccta | atgagtgagc | 180 |
| taactcacat | taattgcgtt | gcgctcactg | cccgctttcc | agtcgggaaa | cctgtcgtgc | 240 |
| cagctgcatt | aatgaatcgg | ccaacgcgcg | gggagaggcg | gtttgcgtat | tgggcgctct | 300 |
| tccgcttcct | cgctcactga | ctcgctgcgc | tcggtcgttc | ggctgcggcg | agcggtatca | 360 |
| gctcactcaa | aggcggtaat | acggttatcc | acagaatcag | gggataacgc | aggaaagaac | 420 |
| atgtgagcaa | aaggccagca | aaaggccagg | aaccgtaaaa | aggccgcgtt | gctggcgttt | 480 |
| ttccataggc | tccgcccccc | tgacgagcat | cacaaaaatc | gacgctcaag | tcagaggtgg | 540 |
| cgaaacccga | caggactata | aagataccag | gcgtttcccc | ctggaagctc | cctcgtgcgc | 600 |
| tctcctgttc | cgaccctgcc | gcttaccgga | tacctgtccg | cctttctccc | ttcgggaagc | 660 |
| gtggcgcttt | ctcatagctc | acgctgtagg | tatctcagtt | cggtgtaggt | cgttcgctcc | 720 |
| aagctgggct | gtgtgcacga | accccccgtt | cagcccgacc | gctgcgcctt | atccggtaac | 780 |
| tatcgtcttg | agtccaaccc | ggtaagacac | gacttatcgc | cactggcagc | agccactggt | 840 |
| aacaggatta | gcagagcgag | gtatgtaggc | ggtgctacag | agttcttgaa | gtggtggcct | 900 |
| aactacggct | acactagaag | gacagtattt | ggtatctgcg | ctctgctgaa | gccagttacc | 960 |
| ttcggaaaaa | gagttggtag | ctcttgatcc | ggcaaacaaa | ccaccgctgg | tagcggtggt | 1020 |
| ttttttgttt | gcaagcagca | gattacgcgc | agaaaaaaag | gatctcaaga | agatcctttg | 1080 |
| atcttttcta | cggggtctga | cgctcagtgg | aacgaaaact | cacgttaagg | gattttggtc | 1140 |
| atgagattat | caaaaaggat | cttcacctag | atccttttaa | attaaaaatg | aagttttaaa | 1200 |
| tcaatctaaa | gtatatatga | gtaaacttgg | tctgacagtt | accaatgctt | aatcagtgag | 1260 |
| gcacctatct | cagcgatctg | tctatttcgt | tcatccatag | ttgcctgact | ccccgtcgtg | 1320 |
| tagataacta | cgatacggga | gggcttacca | tctggcccca | gtgctgcaat | gataccgcga | 1380 |
| gacccacgct | caccggctcc | agatttatca | gcaataaacc | agccagccgg | aagggccgag | 1440 |
| cgcagaagtg | gtcctgcaac | tttatccgcc | tccatccagt | ctattaattg | ttgccgggaa | 1500 |
| gctagagtaa | gtagttcgcc | agttaatagt | ttgcgcaacg | ttgttgccat | tgctacaggc | 1560 |
| atcgtggtgt | cacgctcgtc | gtttggtatg | gcttcattca | gctccggttc | caacgatca | 1620 |
| aggcgagtta | catgatcccc | catgttgtgc | aaaaaagcgg | ttagctcctt | cggtcctccg | 1680 |
| atcgttgtca | gaagtaagtt | ggccgcagtg | ttatcactca | tggttatggc | agcactgcat | 1740 |
| aattctctta | ctgtcatgcc | atccgtaaga | tgcttttctg | tgactggtga | gtactcaacc | 1800 |
| aagtcattct | gagaatagtg | tatgcggcga | ccgagttgct | cttgcccggc | gtcaatacgg | 1860 |
| gataataccg | cgccacatag | cagaacttta | aaagtgctca | tcattggaaa | acgttcttcg | 1920 |

-continued

```
gggcgaaaac tctcaaggat cttaccgctg ttgagatcca gttcgatgta acccactcgt    1980
gcacccaact gatcttcagc atcttttact ttcaccagcg tttctgggtg agcaaaaaca    2040
ggaaggcaaa atgccgcaaa aagggaata agggcgacac ggaaatgttg aatactcata    2100
ctcttccttt ttcaatatta ttgaagcatt tatcagggtt attgtctcat gagcggatac    2160
atatttgaat gtatttagaa aaataaacaa ataggggttc cgcgcacatt tccccgaaaa    2220
gtgccaccta aattgtaagc gttaatattt tgttaaaatt cgcgttaaat ttttgttaaa    2280
tcagctcatt ttttaaccaa taggccgaaa tcggcaaaat cccttataaa tcaaaagaat    2340
agaccgagat agggttgagt gttgttccag tttggaacaa gagtccacta ttaaagaacg    2400
tggactccaa cgtcaaaggg cgaaaaaccg tctatcaggg cgatggccca ctacgtgaac    2460
catcacccta atcaagtttt tggggtcga ggtgccgtaa agcactaaat cggaaccccta    2520
aagggagccc ccgatttaga gcttgacggg gaaagccggc gaacgtggcg agaaaggaag    2580
ggaagaaagc gaaaggagcg ggcgctaggg cgctggcaag tgtagcggtc acgctgcgcg    2640
taaccaccac acccgccgcg cttaatgcgc cgctacaggg cgcgtcccat tcgccattca    2700
ggctgcgcaa ctgttgggaa gggcgatcgg tgcgggcctc ttcgctatta cgccagctgg    2760
cgaaaggggg atgtgctgca aggcgattaa gttgggtaac gccagggttt tcccagtcac    2820
gacgttgtaa aacgacggcc agtgagcgcg cgtaatacga ctcactatag gcgaattgg    2880
agctccaccg cggtggcggc cgctctagaa ctagtggatc cgtcgactag agggcccgac    2940
gtcgaactta ggcactaagg gatgtgaggc cagcatcacc gttgcagaaa ttgacacaag    3000
catcaccaca attttccaaa tagagtttca tttcttcgtc gtcagcagct gcgttgacca    3060
tgtagtcaca catggaagcc ctacacccca agttgcaata cttgacggtg tctggttcat    3120
ctgagttgga cacaagggcc aatttgggga agcctgtagg gcattttccg ctacttgtga    3180
gtttacacct acagacgcct gcgcataact tctgagcacc acggacgcgg caaaggttgt    3240
agcagtttct tcctagggtg ctcctgcagc aactcttgcc ttctacttgc acctgttcga    3300
gaaccaaccc cagtataagt aaacacacca tcacaccctt gaggcccttg ctggtggcca    3360
tgg                                                                  3363
```

<210> SEQ ID NO 2
<211> LENGTH: 3365
<212> TYPE: DNA
<213> ORGANISM: Artificial Sequence
<220> FEATURE:
<223> OTHER INFORMATION: pBSKP vector with a modified gene based on
      Hordeum vulgare located from nucleotide 3361 to nucleotide 2947.

<400> SEQUENCE: 2

```
tcgacctcga ggggggggccc ggtacccagc ttttgttccc tttagtgagg gttaattgcg      60
cgcttggcgt aatcatggtc atagctgttt cctgtgtgaa attgttatcc gctcacaatt     120
ccacacaaca tacgagccgg aagcataaag tgtaaagcct ggggtgccta atgagtgagc     180
taactcacat taattgcgtt gcgctcactg cccgctttcc agtcgggaaa cctgtcgtgc     240
cagctgcatt aatgaatcgg ccaacgcgcg gggagaggcg gtttgcgtat tgggcgctct     300
tccgcttcct cgctcactga ctcgctgcgc tcggtcgttc ggctgcggcg agcggtatca     360
gctcactcaa aggcggtaat acggttatcc acagaatcag gggataacgc aggaaagaac     420
atgtgagcaa aaggccagca aaaggccagg aaccgtaaaa aggccgcgtt gctggcgttt     480
ttccataggc tccgcccccc tgacgagcat cacaaaaatc gacgctcaag tcagaggtgg     540
```

```
cgaaacccga caggactata aagataccag gcgtttcccc ctggaagctc cctcgtgcgc      600
tctcctgttc cgaccctgcc gcttaccgga tacctgtccg cctttctccc ttcgggaagc      660
gtggcgcttt ctcatagctc acgctgtagg tatctcagtt cggtgtaggt cgttcgctcc      720
aagctgggct gtgtgcacga acccccgtt cagcccgacc gctgcgcctt atccggtaac       780
tatcgtcttg agtccaaccc ggtaagacac gacttatcgc cactggcagc agccactggt      840
aacaggatta gcagagcgag gtatgtaggc ggtgctacag agttcttgaa gtggtggcct      900
aactacggct acactagaag gacagtattt ggtatctgcg ctctgctgaa gccagttacc      960
ttcggaaaaa gagttggtag ctcttgatcc ggcaaacaaa ccaccgctgg tagcggtggt     1020 tttttttgttt gcaagcagca gattacgcgc agaaaaaaag gatctcaaga agatcctttg     1080
atcttttcta cggggtctga cgctcagtgg aacgaaaact cacgttaagg gattttggtc     1140
atgagattat caaaaaggat cttcacctag atccttttaa attaaaaatg aagttttaaa     1200
tcaatctaaa gtatatatga gtaaacttgg tctgacagtt accaatgctt aatcagtgag     1260
gcacctatct cagcgatctg tctatttcgt tcatccatag ttgcctgact ccccgtcgtg     1320
tagataacta cgatacggga gggcttacca tctggcccca gtgctgcaat gataccgcga     1380
gacccacgct caccggctcc agatttatca gcaataaacc agccagccgg aagggccgag     1440
cgcagaagtg gtcctgcaac tttatccgcc tccatccagt ctattaattg ttgccgggaa     1500
gctagagtaa gtagttcgcc agttaatagt ttgcgcaacg ttgttgccat gctacaggc      1560 atcgtggtgt cacgctcgtc gtttggtatg gcttcattca gctccggttc ccaacgatca     1620
aggcgagtta catgatcccc catgttgtgc aaaaaagcgg ttagctcctt cggtcctccg     1680
atcgttgtca gaagtaagtt ggccgcagtg ttatcactca tggttatggc agcactgcat     1740
aattctctta ctgtcatgcc atccgtaaga tgcttttctg tgactggtga gtactcaacc     1800
aagtcattct gagaatagtg tatgcggcga ccgagttgct cttgcccggc gtcaatacgg     1860
gataataccg cgccacatag cagaacttta aaagtgctca tcattggaaa acgttcttcg     1920
gggcgaaaac tctcaaggat cttaccgctg ttgagatcca gttcgatgta acccactcgt     1980
gcacccaact gatcttcagc atcttttact ttcaccagcg tttctgggtg agcaaaaaca     2040
ggaaggcaaa atgccgcaaa aaagggaata agggcgacac ggaaatgttg aatactcata     2100
ctcttccttt ttcaatatta ttgaagcatt tatcagggtt attgtctcat gagcggatac     2160
atatttgaat gtatttagaa aaataaacaa ataggggttc cgcgcacatt tccccgaaaa     2220
gtgccaccta aattgtaagc gttaatattt tgttaaaatt cgcgttaaat ttttgttaaa     2280
tcagctcatt ttttaaccaa taggccgaaa tcggcaaaat cccttataaa tcaaaagaat     2340
agaccgagat agggttgagt gttgttccag tttggaacaa gagtccacta ttaaagaacg     2400
tggactccaa cgtcaaaggg cgaaaaaccg tctatcaggg cgatggccca ctacgtgaac     2460
catcacccta atcaagtttt tgggggtcga ggtgccgtaa agcactaaat cggaaccta     2520 aagggagccc ccgatttaga gcttgacggg gaaagccggc gaacgtggcg agaaaggaag     2580
ggaagaaagc gaaaggagcg ggcgctaggg cgctggcaag tgtagcggtc acgctgcgcg     2640
taaccaccac acccgccgcg cttaatgcgc cgctacaggg cgcgtcccat cgccattca      2700 ggctgcgcaa ctgttgggaa gggcgatcgg tgcgggcctc ttcgctatta cgccagctgg     2760
cgaaaggggg atgtgctgca aggcgattaa gttgggtaac gccagggttt tcccagtcac     2820
gacgttgtaa aacgacggcc agtgagcgcg cgtaatacga ctcactatag gcgaattgg      2880 agctccaccg cggtggcggc cgctctagaa ctagtggatc cgtcgactag agggcccgac     2940
```

```
gtcgaactta ggcactaagg gatgtgaggc cagcatcacc gttgcagaaa ttgacacaag    3000
catcaccaca atttccaaa tagagttca tttcttcgtc gtcagcagct gcgttgacca    3060
tgtagtcaca catggaagcc ctacacccca agttgcaata cttgacggtg tctggttcat    3120
ctgagttgga cacaagggcc aatttgggga agcctttcgg gcattttccg ctactagtca    3180
gcttacactt gcagacgcct gcgcaaagct tcttggcgcc tttgactttg caaaggttgt    3240
agcacttcct tcccagggta ctcttgcagc aactcttgcc ttctacttgc acctgttcga    3300
gaaccaaccc cagtataagt aaacacacca tcacacccctt gaggcccttg ctggtggcca    3360
tggtg                                                                3365

<210> SEQ ID NO 3
<211> LENGTH: 5360
<212> TYPE: DNA
<213> ORGANISM: Artificial Sequence
<220> FEATURE:
<223> OTHER INFORMATION: Modified gene based on Hordeum vulgare from
      nucleotide 2199 to nucleotide 2612 in Zea mays expression vector.
      Zea mays promoter from nucleotide 676 to nucleotide 2198.

<400> SEQUENCE: 3
ctaaattgta agcgttaata ttttgttaaa attcgcgtta aattttgtt aaatcagctc      60 attttttaac caataggccg aaatcggcaa atcccttat aaatcaaaag aatagaccga    120 gataggggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcggggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gattatataa tttataagct aaacaacccg gccctaaagc    720
actatcgtat cacctatcta aataagtcac gggagtttcg aacgtccact tcgtcgcacg    780
gaattgcatg ttctcttgttg gaagcatatt cacgcaatct ccacacataa aggtttatgt    840
ataaacttac atttagctca gttaattac agtcttattt ggatgcatat gtatggttct    900
caatccatat aagttagagt aaaaaataag tttaattttt atcttaattc actccaacat    960
atatggatct acaatactca tgtgcatcca acaaactac ttatattgag gtgaatttgg   1020
tagaaattaa actaacttac acactaagcc aatctttact atattaaagc accagtttca    1080
acgatcgtcc cgcgtcaata ttataaaaa actcctacat ttctttataa tcaacccgca    1140 ctcttatat ctcttctcta ctactataat aagagagttt atgtacaaaa taaggtgaaa    1200
ttatctataa gtgttctgga tattggttgt tggctcccat attcacacaa cctaatcaat    1260
agaaaacata tgtttttatta aaacaaaaatt tatcatatat catatatata tatatatcat    1320
atatatatat aaaccgtagc aatgcacggg catataacta gtgcaactta atacatgtgt    1380
gtattaagat gaataagagg gtatccaaat aaaaaacttg ttgcttacgt atggatcgaa    1440
aggggttgga aacgattaaa cgattaaatc tcttcctagt caaaattgaa tagaaggaga    1500
tttaatatat cccaatcccc ttcgatcatc caggtgcaac cgtataagtc ctaaagtggt    1560
```

-continued

```
gaggaacacg aaagaaccat gcattggcat gtaaagctcc aagaatttgt tgtatcctta    1620
acaactcaca gaacatcaac caaaattgca cgtcaagggt attgggtaag aaacaatcaa    1680
acaaatcctc tctgtgtgca agaaacacg gtgagtcatg ccgagatcat actcatctga     1740
tatacatgct tacagctcac aagacattac aaacaactca tattgcatta caaagatcgt    1800
ttcatgaaaa ataaaatagg ccggacagga caaaaatcct tgacgtgtaa agtaaattta    1860
caacaaaaaa aaagccatat gtcaagctaa atctaattcg tttacgtag atcaacaacc     1920 tgtagaaggc aacaaaactg agccacgcag aagtacagaa tgattccaga tgaaccatcg    1980
acgtgctacg taaagagagt gacgagtcat atacatttgg caagaaacca tgaagctgcc    2040
tacagccgtc tcggtggcat aagaacacaa gaaattgtgt taattaatca aagctataaa    2100
taacgctcgc atgcctgtgc acttctccat caccaccact gggtcttcag accattagct    2160
ttatctactc cagagcgcag aagaacccga tcgacaccat ggccaccagc aagggcctca    2220
agggtgtgat ggtgtgttta cttatactgg ggttggttct cgaacaggtg caagtagaag    2280
gcaagagttg ctgcaagagt accctgggaa ggaagtgcta caacctttgc aaagtcaaag    2340
gcgccaagaa gctttgcgca ggcgtctgca agtgtaagct gactagtagc ggaaaatgcc    2400
cgaaaggctt ccccaaattg gcccttgtgt ccaactcaga tgaaccagac accgtcaagt    2460
attgcaactt ggggtgtagg gcttccatgt gtgactacat ggtcaacgca gctgctgacg    2520
acgaagaaat gaaactctat ttggaaaatt gtggtgatgc ttgtgtcaat ttctgcaacg    2580
gtgatgctgg cctcacatcc cttagtgcct aagttcgacg tcgggccctc tagtcgacgg    2640
atccccggcg gtgtccccca ctgaagaaac tatgtgctgt agtatagccg ctgcccgctg    2700
gctagctagc tagttgagtc atttagcggc gatgattgag taataatgtg tcacgcatca    2760
ccatgcatgg gtggcagtgt cagtgtgagc aatgacctga atgaacaatt gaaatgaaaa    2820
gaaaaaagta ttgttccaaa ttaaacgttt taaccttta ataggtttat acaataattg      2880
atatatgttt tctgtatatg tctaatttgt tatcatccat ttagatatag acaaaaaaaa    2940
atctaagaac taaacaaat gctaatttga aatgaaggga gtatatattg ggataatgtc     3000
gatgagatcc ctcgtaatat caccgacatc acacgtgtcc agttaatgta tcagtgatac    3060
gtgtattcac atttgttgcg cgtaggcgta cccaacaatt ttgatcgact atcagaaagt    3120
caacggaagc gagtcgacct cgagggggg cccggtaccc agcttttgtt ccctttagtg      3180
agggttaatt gcgcgcttgg cgtaatcatg gtcatagctg tttcctgtgt gaaattgtta    3240
tccgctcaca attccacaca acatacgagc cggaagcata aagtgtaaag cctggggtgc    3300
ctaatgagtg agctaactca cattaattgc gttgcgctca ctgcccgctt tccagtcggg    3360
aaacctgtcg tgccagctgc attaatgaat cggccaacgc gcggggagag gcggtttgcg    3420
tattgggcgc tcttccgctt cctcgctcac tgactcgctg cgctcggtcg ttcggctgcg    3480
gcgagcggta tcagctcact caaaggcggt aatacggtta tccacagaat cagggggataa    3540 cgcaggaaag aacatgtgag caaaaggcca gcaaaaggcc aggaaccgta aaaaggccgc    3600
gttgctggcg ttttttccata ggctccgccc ccctgacgag catcacaaaa atcgacgctc    3660
aagtcagagg tggcgaaacc cgacaggact ataaagatac caggcgtttc ccctggaag    3720 ctccctcgtg cgctctcctg ttccgaccct gccgcttacc ggatacctgt ccgcctttct    3780
cccttcggga agcgtggcgc tttctcatag ctcacgctgt aggtatctca gttcggtgta    3840
ggtcgttcgc tccaagctgg gctgtgtgca cgaaccccc gttcagcccg accgctgcgc      3900
cttatccggt aactatcgtc ttgagtccaa cccggtaaga cacgacttat cgccactggc    3960
```

-continued

```
agcagccact ggtaacagga ttagcagagc gaggtatgta ggcggtgcta cagagttctt     4020
gaagtggtgg cctaactacg gctacactag aaggacagta tttggtatct gcgctctgct     4080
gaagccagtt accttcggaa aaagagttgg tagctcttga tccggcaaac aaaccaccgc     4140
tggtagcggt ggttttttg  tttgcaagca gcagattacg cgcagaaaaa aaggatctca     4200
agaagatcct ttgatctttt ctacggggtc tgacgctcag tggaacgaaa actcacgtta     4260
agggattttg gtcatgagat tatcaaaaag gatcttcacc tagatccttt taaattaaaa     4320
atgaagtttt aaatcaatct aaagtatata tgagtaaact tggtctgaca gttaccaatg     4380
cttaatcagt gaggcaccta tctcagcgat ctgtctattt cgttcatcca tagttgcctg     4440
actccccgtc gtgtagataa ctacgatacg ggagggctta ccatctggcc ccagtgctgc     4500
aatgataccg cgagacccac gctcaccggc tccagattta tcagcaataa accagccagc     4560
cggaagggcc gagcgcagaa gtggtcctgc aactttatcc gcctccatcc agtctattaa     4620
ttgttgccgg gaagctagag taagtagttc gccagttaat agtttgcgca acgttgttgc     4680
cattgctaca ggcatcgtgg tgtcacgctc gtcgtttggt atggcttcat tcagctccgg     4740
ttcccaacga tcaaggcgag ttacatgatc ccccatgttg tgcaaaaaag cggttagctc     4800
cttcggtcct ccgatcgttg tcagaagtaa gttggccgca gtgttatcac tcatggttat     4860
ggcagcactg cataattctc ttactgtcat gccatccgta agatgctttt ctgtgactgg     4920
tgagtactca accaagtcat tctgagaata gtgtatgcgg cgaccgagtt gctcttgccc     4980
ggcgtcaata cgggataata ccgcgccaca tagcagaact ttaaaagtgc tcatcattgg     5040
aaaacgttct cgggggcgaa aactctcaag gatcttaccg ctgttgagat ccagttcgat     5100
gtaacccact cgtgcaccca actgatcttc agcatctttt actttcacca gcgtttctgg     5160
gtgagcaaaa acaggaaggc aaaatgccgc aaaaaaggga ataagggcga cacggaaatg     5220
ttgaatactc atactcttcc tttttcaata ttattgaagc attatcagg  gttattgtct     5280 catgagcgga tacatatttg aatgtattta gaaaaataaa caaataggg  ttccgcgcac     5340 atttccccga aaagtgccac                                                  5360
```

<210> SEQ ID NO 4
<211> LENGTH: 5511
<212> TYPE: DNA
<213> ORGANISM: Artificial Sequence
<220> FEATURE:
<223> OTHER INFORMATION: Modified gene based on Hordeum vulgare from
      nucleotide 1834 to nucleotide 1420 in Zea mays expression vector.
      Zea mays promoter from nucleotide 3271 to nucleotide 1834.

<400> SEQUENCE: 4

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg  cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cttttatgaa taataataat      420
gcatatctgt gcattactac ctgggataca agggcttctc cgccataaca aattgagttg      480
cgatgctgag aacgaacggg gaagaaagta agcgccgccc aaaaaaaacg aacatgtacg      540
tcggctatag caggtgaaag ttcgtgcgcc aatgaaaagg gaacgatatg cgttgggtag      600
```

-continued

| | |
|---|---|
| ttgggatact taaatttgga gagtttgttg catacactaa tccactaaag ttgtctatct | 660 |
| ttttaacagc tctaggcagg atataagatt tatatctaat ctgttggagt tgcttttaga | 720 |
| gtaacttttc tctctgtttc gtttatagcc gattagcaca aaattaaact aggtgacgag | 780 |
| aaataaagaa aaacggaggc agtaaaaaat acccaaaaaa atacttggag attttttgtct | 840 |
| caaaattatc ttctaatttt aaaagctaca tattaaaaat actatatatt aaaaatactt | 900 |
| cgagatcatt gcttgggatg gcagggcca atagctaatt gctaaggatg gctatatttt | 960 |
| atgtatcgtc tgaaacatgt aggggctaat agttagatga ctaatttgct gtgttcgtac | 1020 |
| ggggtgctgt ttgagcctag cgatgaaggg tcatagtttc atacaagaac tcacttttgg | 1080 |
| ttcgtctgct gtgtctgttc tcagcgtaac ggcatcaatg gatgccaaac tccgcaaggg | 1140 |
| gacaaatgaa gaagcgaaga gattatagaa cacgcacgtg tcattattta tttatggact | 1200 |
| tgcctcagta gcttacagca tcgtacccgc acgtacatac tacagagcca cacttattgc | 1260 |
| actgcctgcc gcttacgtac atagttaaca cgcagagagg tatatacata cacgtccaac | 1320 |
| gtctccactc aggctcatgc tacgtacgca cgtcggtcgc gcgccaccct ctcgttgctt | 1380 |
| cctgctcgtt ttggcgagct agagggcccg acgtcgaact taggcactaa gggatgtgag | 1440 |
| gccagcatca ccgttgcaga aattgacaca agcatcacca caattttcca aatagagttt | 1500 |
| catttcttcg tcgtcagcag ctgcgttgac catgtagtca cacatggaag ccctacaccc | 1560 |
| caagttgcaa tacttgacgg tgtctggttc atctgagttg gacacaaggg ccaatttggg | 1620 |
| gaagcctttc gggcattttc cgctactagt cagcttacac ttgcagacgc ctgcgcaaag | 1680 |
| cttcttggcg cctttgactt tgcaaaggtt gtagcacttc cttcccaggg tactcttgca | 1740 |
| gcaactcttg ccttctactt gcacctgttc gagaaccaac cccagtataa gtaaacacac | 1800 |
| catcacaccc ttgaggccct tgctggtggc catggtgtag tgtcgactgt gatatcctcg | 1860 |
| ggtgtgtgtt ggatccttgg gttggctgta tgcagaacta aagcggaggt ggcgcgcatt | 1920 |
| tataccagcg ccgggccctg gtacgtggcg cggccgcgcg gctacgtgga ggaaggctgc | 1980 |
| gtggcagcag acacacgggt cgccacgtcc cgccgtactc tccttaccgt gcttatccgg | 2040 |
| gctccggctc ggtgcacgcc agggtgtggc cgcctctgag cagactttgt cgtgttccac | 2100 |
| agtggtgtcg tgttccgggg actccgatcc gcggcgagcg accgagcgtg taaaagagtt | 2160 |
| cctactaggt acgttcattg tatctggacg acgggcagcg gacaatttgc tgtaagagag | 2220 |
| gggcagtttt ttttttagaaa aacagagaat tccgttgagc taattgtaat tcaacaaata | 2280 |
| agctattagt tggttttagc ttagattaaa gaagctaacg actaatagct aataattagt | 2340 |
| tggtctatta gttgactcat tttaaggccc tgtttcaatc tcgcgagata aactttagca | 2400 |
| gctatttttt agctacttttt agccatttgt aatctaaaca ggagagctaa tggtggtaat | 2460 |
| tgaaactaaa ctttagcact tcaattcata tagctaaagt ttagcaggaa gctaaacttt | 2520 |
| atcccgtgag attgaaacgg ggcctaaatc tctcagctat ttttgatgca aattactgtc | 2580 |
| actactggaa tcgagcgctt tgccgagtgt caaagcctga aaaacactcc gtaaagactt | 2640 |
| tgcctagtgt gacactcgac aaagagatct cgacgaacag tacatcgaca acggcttctt | 2700 |
| tgtcgagtac tttttatcgg acacttgaca aagtctttgt cgagtgaact acattgaaac | 2760 |
| tctatgattt tatgtgtagg tcacttaggt ttctacacat agtacgtcac aactttaccg | 2820 |
| aaacattatc aaatttttat cacaacctct atatatgata tcatgacatg tggacaagtt | 2880 |
| tcattaattt ctgactttat ttgtgttta tacaattttt aaacaactag ataacaagtt | 2940 |
| cacggtcatg tttagtgagc atggtgcttg aagattctgg tctgcttctg aaatcggtcg | 3000 |

```
taacttgtgc tagataacat gcatatcatt tattttgcat gcacggtttt ccatgtttcg    3060
agtgacttgc agtttaaatg tgaattttcc gaagaaattc aaataaacga actaaatcta    3120
atatttatag aaaacatttt tgtaaatatg taattgtgcc aaaatggtac atgtagatct    3180
acatagtgta ggaacatacc acaaaaagtt tggttggcaa aataaaaaaa ataaaatata    3240
ctttatcgag tgtccaagga tggcactcgg caagcttggc gtaatcatgg tcatagctgt    3300
ttcctgtgtg aaattgttat ccgctcacaa ttccacacaa catacgagcc ggaagcataa    3360
agtgtaaagc ctggggtgcc taatgagtga gctaactcac attaattgcg ttgcgctcac    3420
tgcccgcttt ccagtcggga acctgtcgt gccagctgca ttaatgaatc ggccaacgcg    3480
cggggagagg cggtttgcgt attgggcgct cttccgcttc ctcgctcact gactcgctgc    3540
gctcggtcgt tcggctgcgg cgagcggtat cagctcactc aaaggcggta atacggttat    3600
ccacagaatc aggggataac gcaggaaaga acatgtgagc aaaaggccag caaaaggcca    3660
ggaaccgtaa aaaggccgcg ttgctggcgt ttttccatag gctccgcccc cctgacgagc    3720
atcacaaaaa tcgacgctca agtcagaggt ggcgaaaccc gacaggacta taaagatacc    3780
aggcgtttcc ccctggaagc tccctcgtgc gctctcctgt tccgaccctg ccgcttaccg    3840
gatacctgtc cgcctttctc ccttcgggaa gcgtggcgct ttctcaatgc tcacgctgta    3900
ggtatctcag ttcggtgtag tcgttcgct ccaagctggg ctgtgtgcac gaaccccccg    3960
ttcagcccga ccgctgcgcc ttatccggta actatcgtct tgagtccaac ccggtaagac    4020
acgacttatc gccactggca gcagccactg gtaacaggat tagcagagcg aggtatgtag    4080
gcggtgctac agagttcttg aagtggtggc ctaactacgg ctacactaga aggacagtat    4140
ttggtatctg cgctctgctg aagccagtta ccttcggaaa aagagttggt agctcttgat    4200
ccggcaaaca aaccaccgct ggtagcggtg gttttttgt ttgcaagcag cagattacgc    4260
gcagaaaaaa aggatctcaa gaagatcctt tgatcttttc tacggggtct gacgctcagt    4320
ggaacgaaaa ctcacgttaa gggattttgg tcatgagatt atcaaaaagg atcttcacct    4380
agatcctttt aaattaaaaa tgaagtttta atcaatcta agtatatat gagtaaactt    4440 ggtctgacag ttaccaatgc ttaatcagtg aggcacctat ctcagcgatc tgtctatttc    4500
gttcatccat agttgcctga ctccccgtcg tgtagataac tacgacggg gagggcttac    4560 catctggccc cagtgctgca atgataccgc gagacccacg ctcaccggct ccagatttat    4620
cagcaataaa ccagccagcc ggaagggccg agcgcagaag tggtcctgca actttatccg    4680
cctccatcca gtctattaat tgttgccggg aagctagagt aagtagttcg ccagttaata    4740
gtttgcgcaa cgttgttgcc attgctacag gcatcgtggt gtcacgctcg tcgtttggta    4800
tggcttcatt cagctccggt tcccaacgat caaggcgagt tacatgatcc cccatgttgt    4860
gcaaaaaagc ggttagctcc ttcggtcctc cgatcgttgt cagaagtaag ttggccgcag    4920
tgttatcact catggttatg gcagcactgc ataattctct tactgtcatg ccatccgtaa    4980
gatgcttttc tgtgactggt gagtactcaa ccaagtcatt ctgagaatag tgtatgcggc    5040
gaccgagttg ctcttgcccg gcgtcaatac gggataatac cgcgccacat agcagaactt    5100
taaaagtgct catcattgga aaacgttctt cggggcgaaa actctcaagg atcttaccgc    5160
tgttgagatc cagttcgatg taacccactc gtgcacccaa ctgatcttca gcatcttta    5220 ctttcaccag cgtttctggg tgagcaaaaa caggaaggca aaatgccgca aaaaagggaa    5280
taagggcgac acgaaatgt tgaatactca tactcttcct ttttcaatat tattgaagca    5340
tttatcaggg ttattgtctc atgagcggat acatatttga atgtatttag aaaaataaac    5400
```

-continued

| | |
|---|---|
| aaatagggt tccgcgcaca ttttccccgaa aagtgccacc tgacgtctaa gaaaccatta | 5460 |
| ttatcatgac attaacctat aaaaataggc gtatcacgag gccctttcgt c | 5511 |

<210> SEQ ID NO 5
<211> LENGTH: 5115
<212> TYPE: DNA
<213> ORGANISM: Artificial Sequence
<220> FEATURE:
<223> OTHER INFORMATION: Gene from Hordeum vulgare from nucleotide 1343
      to nucleotide 1757 in Zea mays expression vector. Zea mays
      promoter from nucleotide 43 to nucleotide 1342.

<400> SEQUENCE: 5

| | |
|---|---|
| gttgggagct ctcccatatg gtcgacctgc aggcggccgc tctagaacta gtggatcccc | 60 |
| ccctcgaggt cgacggtatc gataagcttg atatcttaca aggcccagcc cagcgaccta | 120 |
| ttacacagcc cgctcgggcc cgcgacgtcg ggacacatct tcttccccct tttggtgaag | 180 |
| ctctgctcgc agctgtccgg ctccttggac gttcgtgtgg cagattcatc tgttgtctcg | 240 |
| tctcctgtgc ttcctgggta gcttgtgtag tggagctgac atggtctgag caggcttaaa | 300 |
| atttgctcgt agacgaggag taccagcaca gcacgttgcg gatttctctg cctgtgaagt | 360 |
| gcaacgtcta ggattgtcac acgccttggt cgcgtcgcgt cgcgtcgcgt cgatgcggtg | 420 |
| gtgagcagag cagcaacagc tgggcggccc aacgttggct tccgtgtctt cgtcgtacgt | 480 |
| acgcgcgcgc cggggacacg cagcagagag cggagagcga gccgtgcacg gggaggtggt | 540 |
| gtggaagtgg agccgcgcgc ccggccgccc gcgcccggtg ggcaacccaa aagtacccac | 600 |
| gacaagcgaa ggcgccaaag cgatccaagc tccggaacgc aacagcatgc gtcgcgtcgg | 660 |
| agagccagcc acaagcagcc gagaaccgaa ccggtgggcg acgcgtcatg ggacggacgc | 720 |
| gggcgacgct tccaaacggg ccacgtacgc cggcgtgtgc gtgcgtgcag acgacaagcc | 780 |
| aaggcgaggc agccccccgat cgggaaagcg ttttgggcgc gagcgctggc gtgcgggtca | 840 |
| gtcgctggtg cgcagtgccg gggggaacgg gtatcgtggg gggcgcgggc ggaggagagc | 900 |
| gtggcgaggg ccgagagcag cgcgcggccg ggtcacgcaa cgcgccccac gtactgccct | 960 |
| cccctccgc gcgcgctaga aataccgagg cctggaccgg ggggggccc cgtcacatcc | 1020 |
| atccatcgac cgatcgatcg ccacagccaa caccacccgc cgaggcgacg cgacagccgc | 1080 |
| caggaggaag gaataaactc actgccagcc agtgaagggg gagaagtgta ctgctccgtc | 1140 |
| gaccagtgcg cgcaccgccc ggcagggctg ctcatctcgt cgacgaccag gttctgttcc | 1200 |
| gatccgatcc gatcctgtcc ttgagtttcg tccagatcct ggcgcgtatc tgcgtgtttg | 1260 |
| atgatccagg ttcttcgaac ctaaatctgt ccgtgcacac gtctttttctc tctctcctac | 1320 |
| gcagtggatt aatcgccatg gccaccagca agggcctcaa gggtgtgatg gtgtgtttac | 1380 |
| ttatactggg gttggttctc gaacaggtgc aagtagaagg caagagttgc tgcaagagta | 1440 |
| ccctgggaag gaagtgctac aacctttgca aagtcaaagg cgccaagaag ctttgcgcag | 1500 |
| gcgtctgcaa gtgtaagctg actagtagcg gaaaatgccc gaaaggcttc cccaaattgg | 1560 |
| cccttgtgtc caactcagat gaaccagaca ccgtcaagta ttgcaacttg gggtgtaggg | 1620 |
| cttccatgtg tgactacatg gtcaacgcag ctgctgacga cgaagaaatg aaactctatt | 1680 |
| tggaaaattg tggtgatgct tgtgtcaatt tctgcaacgg tgatgctggc ctcacatccc | 1740 |
| ttagtgccta agttcgacgt cgggccctct agatgcggcc cggtgaaga gttcgccctg | 1800 |
| cagggcccct gatctcgcgc gtggtgcaaa gatgttggga catcttctta tatatgctgt | 1860 |
| ttcgcttatg tgatatggac aagtatgtgt agatgcttgc ttgtgctagt gtaatgtagt | 1920 |

```
gtagtggtgg ccagtggcac aacctaataa gcgcatgaac taattgcttg cgtgtgtagt    1980
taagtaccga tcggtaattt tatattgcga gtaaataaat ggacctgtag tggtggagta    2040
aataatccct gctgttcggt gttcttatcg ctcctcgtat agatattata tagagtacat    2100
ttttctctct ctgaatccta cgtgtgtgaa atttctatat cattactgta aaatttctgc    2160
gttccaaaag agaccatagc ctatctttgg ccctgtttgt ttcggcttct ggcagcttct    2220
ggccaccaaa agctgctgcg gactgccaaa cgctcagatt ttcagctagc ttctataaaa    2280
ttagttgggg caaaaaccat ccaaaatcaa tataaacaca taatcggttg agtcgttgta    2340
atattaggaa tctgtcactt tctagatcct gagccctatg aacaacttta tctttctcca    2400
tacgtaatcg taatgatact cagattctct ccacagccag attctcctca cagccagatt    2460
ttcagaaaag ctggtcagaa aaagttaaaa ccaaacagac cctttgtgta tgcatggatc    2520
ggctttcccc gtcaagctct aaatcggggg ctccctttag ggttccgatt tagagcttta    2580
cggcacctcg accgcaaaaa acttgatttg ggtgatggtt cacgtagtgg gccatcgccc    2640
tgatagacgg ttttcgccc tttgacgttg gagtccacgt tctttaatag tggactcttg    2700
ttccaaactg gaacaacact caaccctatc tcggtctatt cttttgattt ataagggatt    2760
ttgccgattt cggcctattg gttaaaaaat gagctgattt aacaaatatt taacgcgaat    2820
tttaacaaaa tattaacgtt tacaatttcg cctgatgcgg tattttctcc ttacgcatct    2880
gtgcggtatt tcacaccgca tacaggtggc acttttcggg gaaatgtgcg cggaaccect    2940 atttgtttat ttttctaaat acattcaaat atgtatccgc tcatgagaca ataaccctga    3000
taaatgcttc aataatattg aaaaaggaag agtatgagta ttcaacattt ccgtgtcgcc    3060
cttattccct tttttgcggc attttgcctt cctgttttg ctcacccaga aacgctggtg    3120
aaagtaaaag atgctgaaga tcagttgggt gcacgagtgg gttacatcga actggatctc    3180
aacagcggta agatccttga gagttttcgc cccgaagaac gttttccaat gatgagcact    3240
tttaaagttc tgctatgtca tacactatta tcccgtattg acgccgggca agagcaactc    3300
ggtcgccggg cgcggtattc tcagaatgac ttggttgagt actcaccagt cacagaaaag    3360
catcttacgg atggcatgac agtaagagaa ttatgcagtg ctgccataac catgagtgat    3420
aacactgcgg ccaacttact tctgacaacg atcggaggac cgaaggagct aaccgctttt    3480
ttgcacaaca tgggggatca tgtaactcgc cttgatcgtt gggaaccgga gctgaatgaa    3540
gccataccaa acgacgagcg tgacaccacg atgcctgtag caatggcaac aacgttgcgc    3600
aaactattaa ctggcgaact acttactcta gcttcccggc aacaattaat agactggatg    3660
gaggcggata agttgcagg accacttctg cgctcggccc ttccggctgg ctggtttatt    3720
gctgataaat ctggagccgg tgagcgtggg tctcgcggta tcattgcagc actggggcca    3780
gatggtaagc cctcccgtat cgtagttatc tacacgacgg ggagtcaggc aactatggat    3840
gaacgaaata gacagatcgc tgagataggt gcctcactga ttaagcattg gtaactgtca    3900
gaccaagttt actcatatat actttagatt gatttaaaac ttcattttta atttaaaagg    3960
atctaggtga agatcctttt tgataatctc atgaccaaaa tcccttaacg tgagttttcg    4020
ttccactgag cgtcagaccc cgtagaaaag atcaaaggat cttcttgaga tcctttttt    4080 ctgcgcgtaa tctgctgctt gcaaacaaaa aaaccaccgc taccagcggt ggtttgtttg    4140
ccggatcaag agctaccaac tcttttttccg aaggtaactg gcttcagcag agcgcagata    4200
ccaaatactg tccttctagt gtagccgtag ttaggccacc acttcaagaa ctctgtagca    4260
ccgcctacat acctcgctct gctaatcctg ttaccagtgg ctgctgccag tggcgataag    4320
```

```
tcgtgtctta ccgggttgga ctcaagacga tagttaccgg ataaggcgca gcggtcgggc    4380
tgaacggggg gttcgtgcac acagcccagc ttggagcgaa cgacctacac cgaactgaga    4440
tacctacagc gtgagctatg agaaagcgcc acgcttcccg aagggagaaa ggcggacagg    4500
tatccggtaa gcggcagggt cggaacagga gagcgcacga gggagcttcc aggggggaaac   4560 gcctggtatc tttatagtcc tgtcgggttt cgccacctct gacttgagcg tcgattttg     4620 tgatgctcgt caggggggcg gagcctatcg aaaaacgcca gcaacgcggc cttttacgg     4680 ttcctggcct tttgctggcc ttttgctcac atgttctttc ctgcgttatc ccctgattct    4740
gtggataacc gtattaccgc ctttgagtga gctgataccg ctcgccgcag ccgaacgacc    4800
gagcgcagcg agtcagtgag cgaggaagcg gaagagcgcc caatacgcaa accgcctctc    4860
cccgcgcgtt ggccgattca ttaatgcagc tggcacgaca ggtttcccga ctggaaagcg    4920
ggcagtgagc gcaacgcaat taatgtgagt tagctcactc attaggcacc ccaggcttta    4980
cactttatgc ttccggctcg tatgttgtgt ggaattgtga gcggataaca atttcacaca    5040
ggaaacagct atgaccatga ttacgccaag ctatttaggt gacactatag aatactcaag    5100
ctatgcatcc aacgc                                                     5115

<210> SEQ ID NO 6
<211> LENGTH: 5392
<212> TYPE: DNA
<213> ORGANISM: Artificial Sequence
<220> FEATURE:
<223> OTHER INFORMATION: Gene from Glycine max from nucleotide 2199 to
      nucleotide 2675 in Zea mays expression vector. Zea mays promoter
      from nucleotide 676 to nucleotide 2198.

<400> SEQUENCE: 6
ctaaattgta agcgttaata ttttgttaaa attcgcgtta aattttgtt aaatcagctc       60 attttttaac caataggccg aaatcggcaa atcccttat aaatcaaaag aatagaccga      120
gatagggttg agtgttgttc cagtttggaa caagagtcca ctattaaaga acgtggactc     180
caacgtcaaa gggcgaaaaa ccgtctatca gggcgatggc ccactacgtg aaccatcacc    240
ctaatcaagt ttttttgggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gattatataa tttataagct aaacaacccg gccctaaagc    720
actatcgtat cacctatcta aataagtcac gggagtttcg aacgtccact tcgtcgcacg    780
gaattgcatg tttcttgttg gaagcatatt cacgcaatct ccacacataa aggtttatgt    840
ataaacttac atttagctca gtttaattac agtcttattt ggatgcatat gtatggttct    900
caatccatat aagttagagt aaaaaataag tttaaatttt atcttaattc actccaacat    960
atatggatct acaatactca tgtgcatcca aacaaactac ttatattgag gtgaatttgg   1020
tagaaattaa actaacttac acactaagcc aatctttact atattaaagc accagtttca   1080
acgatcgtcc cgcgtcaata ttattaaaaa actcctacat ttcttatata tcaacccgca   1140 ctcttatat ctcttctcta ctactataat aagagagttt atgtacaaaa taaggtgaaa    1200
```

-continued

| | | | |
|---|---|---|---|
| ttatctataa gtgttctgga tattggttgt tggctcccat attcacacaa cctaatcaat | 1260 |
| agaaaacata tgttttatta aaacaaaatt tatcatatat catatatata tatatatcat | 1320 |
| atatatatat aaaccgtagc aatgcacggg cataactac gtgcaactta atacatgtgt | 1380 |
| gtattaagat gaataagagg gtatccaaat aaaaaacttg ttgcttacgt atggatcgaa | 1440 |
| agggttgga aacgattaaa cgattaaatc tcttcctagt caaaattgaa tagaaggaga | 1500 |
| tttaatatat cccaatcccc ttcgatcatc caggtgcaac cgtataagtc ctaaagtggt | 1560 |
| gaggaacacg aaagaaccat gcattggcat gtaaagctcc aagaatttgt tgtatcctta | 1620 |
| acaactcaca gaacatcaac caaaattgca cgtcaagggt attgggtaag aaacaatcaa | 1680 |
| acaaatcctc tctgtgtgca aagaaacacg gtgagtcatg ccgagatcat actcatctga | 1740 |
| tatacatgct tacagctcac aagacattac aaacaactca tattgcatta caaagatcgt | 1800 |
| ttcatgaaaa ataaaatagg ccggacagga caaaatcct tgacgtgtaa agtaaattta | 1860 |
| caacaaaaaa aaagccatat gtcaagctaa atctaattcg ttttacgtag atcaacaacc | 1920 |
| tgtagaaggc aacaaaactg agccacgcag aagtacagaa tgattccaga tgaaccatcg | 1980 |
| acgtgctacg taaagagagt gacgagtcat atacatttgg caagaaacca tgaagctgcc | 2040 |
| tacagccgta tcggtggcat aagaacacaa gaaattgtgt taattaatca aagctataaa | 2100 |
| taacgctcgc atgcctgtgc acttctccat caccaccact gggtcttcag accattagct | 2160 |
| ttatctactc cagagcgcag aagaacccga tcgacaccat gaccaagttc acaatcctcc | 2220 |
| tcatctctct tctcttctgc atcgcccaca cttgcagcgc ctccaaatgg cagcaccagc | 2280 |
| aagatagctg ccgcaagcag cttaaggggg tgaacctcac gccctgcgag aagcacatca | 2340 |
| tggagaagat ccaaggccgc ggcgatgacg atgatgatga tgacgacgac aatcacattc | 2400 |
| tcaggaccat gcgggggaag aatcactaca tacggaagaa ggaaggaaaa gacgaagacg | 2460 |
| aagaagaaga aggacacatg cagaagtgct gcgctttgca ctggcatttg gggctcttaa | 2520 |
| gctcgctcat ttctgtgctg cagaagataa tggagaacca gagcgaggaa ctggaggaga | 2580 |
| aggagaagaa gaaatggag aaggagctta tgaacttggc tactatgtgc aggtttgggc | 2640 |
| ccatgatcgg gtgcgacttg tcctccgatg actaagttga tccccggcgg tgtccccac | 2700 |
| tgaagaaact atgtgctgta gtatagccgc tggctagcta gctagttgag tcatttagcg | 2760 |
| gcgatgattg agtaataatg tgtcacgcat caccatgcat gggtggcagt ctcagtgtga | 2820 |
| gcaatgacct gaatgaacaa ttgaaatgaa aagaaaaaag tattgttcca aattaaacgt | 2880 |
| tttaaccttt taataggttt atacaataat tgatatatgt tttctgtata tgtctaattt | 2940 |
| gttatcatcc atttagatat agacgaaaaa aaatctaaga actaaaacaa atgctaattt | 3000 |
| gaaatgaagg gagtatatat tgggataatg tcgatgagat ccctcgtaat atcaccgaca | 3060 |
| tcacacgtgt ccagttaatg tatcagtgat acgtgtattc acatttgttg cgcgtaggcg | 3120 |
| tacccaacaa ttttgatcga ctatcagaaa gtcaacggaa gcgagtcgac ctcgaggggg | 3180 |
| ggcccggtac ccagcttttg ttcccttag tgagggttaa ttgcgcgctt ggcgtaatca | 3240 |
| tggtcatagc tgtttcctgt gtgaaattgt tatccgctca caattccaca caacatacga | 3300 |
| gccggaagca taaagtgtaa agcctggggt gcctaatgag tgagctaact cacattaatt | 3360 |
| gcgttgcgct cactgcccgc tttccagtcg ggaaacctgt cgtgccagct gcattaatga | 3420 |
| atcggccaac gcgcgggag aggcggtttg cgtattgggc gctcttccgc ttcctcgctc | 3480 |
| actgactcgc tgcgctcggt cgttcggctg cggcgagcgg tatcagctca ctcaaaggcg | 3540 |
| gtaatacggt tatccacaga atcaggggat aacgcaggaa agaacatgtg agcaaaaggc | 3600 |

-continued

```
cagcaaaagg ccaggaaccg taaaaaggcc gcgttgctgg cgttttccca taggctccgc    3660 cccctgacg agcatcacaa aaatcgacgc tcaagtcaga ggtggcgaaa cccgacagga     3720
ctataaagat accaggcgtt tccccctgga agctccctcg tgcgctctcc tgttccgacc    3780
ctgccgctta ccggatacct gtccgccttt ctcccttcgg gaagcgtggc gctttctcat    3840
agctcacgct gtaggtatct cagttcggtg taggtcgttc gctccaagct gggctgtgtg    3900
cacgaacccc ccgttcagcc cgaccgctgc gccttatccg gtaactatcg tcttgagtcc    3960
aacccggtaa gacacgactt atcgccactg gcagcagcca ctggtaacag gattagcaga    4020
gcgaggtatg taggcggtgc tacagagttc ttgaagtggt ggcctaacta cggctacact    4080
agaaggacag tatttggtat ctgcgctctg ctgaagccag ttaccttcgg aaaaagagtt    4140
ggtagctctt gatccggcaa acaaaccacc gctggtagcg gtggttttt tgtttgcaag    4200 cagcagatta cgcgcagaaa aaaggatctc aagaagatc ctttgatctt ttctacgggg     4260
tctgacgctc agtggaacga aaactcacgt taagggattt tggtcatgag attatcaaaa    4320
aggatcttca cctagatcct tttaaattaa aaatgaagtt ttaaatcaat ctaaagtata    4380
tatgagtaaa cttggtctga cagttaccaa tgcttaatca gtgaggcacc tatctcagcg    4440
atctgtctat ttcgttcatc catagttgcc tgactccccg tcgtgtagat aactacgata    4500
cgggagggct taccatctgg ccccagtgct gcaatgatac cgcgagaccc acgctcaccg    4560
gctccagatt tatcagcaat aaaccagcca gccggaaggg ccgagcgcag aagtggtcct    4620
gcaactttat ccgcctccat ccagtctatt aattgttgcc gggaagctag agtaagtagt    4680
tcgccagtta atagtttgcg caacgttgtt gccattgcta caggcatcgt ggtgtcacgc    4740
tcgtcgtttg gtatggcttc attcagctcc ggttcccaac gatcaaggcg agttacatga    4800
tcccccatgt tgtgcaaaaa agcggttagc tccttcggtc ctccgatcgt tgtcagaagt    4860
aagttggccg cagtgttatc actcatggtt atggcagcac tgcataattc tcttactgtc    4920
atgccatccg taagatgctt ttctgtgact ggtgagtact caaccaagtc attctgagaa    4980
tagtgtatgc ggcgaccgag ttgctcttgc ccggcgtcaa tacgggataa taccgcgcca    5040
catagcagaa ctttaaaagt gctcatcatt ggaaaacgtt cttcggggcg aaaactctca    5100
aggatcttac cgctgttgag atccagttcg atgtaaccca ctcgtgcacc caactgatct    5160
tcagcatctt ttactttcac cagcgtttct gggtgagcaa aaacaggaag gcaaaatgcc    5220
gcaaaaaagg gaataagggc gacacggaaa tgttgaatac tcatactctt cctttttcaa    5280
tattattgaa gcatttatca gggttattgt ctcatgagcg gatacatatt tgaatgtatt    5340
tagaaaaata acaaataggg gttccgcgc acatttcccc gaaaagtgcc ac              5392
```

<210> SEQ ID NO 7
<211> LENGTH: 5173
<212> TYPE: DNA
<213> ORGANISM: Artificial Sequence
<220> FEATURE:
<223> OTHER INFORMATION: Gene from Hordeum vulgare from nucleotide 2199
to nucleotide 2450 in a Zea mays expression vector. Zea mays
promoter from nucleotide 676 to nucleotide 2198.

<400> SEQUENCE: 7

```
ctaaattgta agcgttaata ttttgttaaa attcgcgtta aattttttgtt aaatcagctc      60 atttttttaac caataggccg aaatcggcaa atcccttat aaatcaaaag aatagaccga      120
gatagggttg agtgttgttc cagttttgaa caagagtcca ctattaaaga acgtggactc      180
caacgtcaaa gggcgaaaaa ccgtctatca gggcgatggc ccactacgtg aaccatcacc      240
```

```
ctaatcaagt tttttggggt cgaggtgccg taaagcacta aatcggaacc ctaaagggag    300 ccccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggt ttttcccagt cacgacgttg    600
taaaacgacg gccagtgagc gcgcgtaata cgactcacta tagggcgaat tggagctcca    660
ccgcggtggc ggccgctcta gattatataa tttataagct aaacaacccg ccctaaagc    720 actatcgtat cacctatcta ataagtcac gggagtttcg aacgtccact tcgtcgcacg    780
gaattgcatg tttcttgttg gaagcatatt cacgcaatct ccacacataa aggtttatgt    840
ataaacttac atttagctca gtttaattac agtcttattt ggatgcatat gtatggttct    900
caatccatat aagttagagt aaaaaataag tttaaatttt atcttaattc actccaacat    960
atatggatct acaatactca tgtgcatcca acaaactac ttatattgag gtgaatttgg   1020
tagaaattaa actaacttac acactaagcc aatctttact atattaaagc accagtttca   1080
acgatcgtcc cgcgtcaata ttattaaaaa actcctacat ttctttataa tcaacccgca   1140
ctcttataat ctcttctcta ctactataat aagagagttt atgtacaaaa taaggtgaaa   1200
ttatctataa gtgttctgga tattggttgt tggctcccat attcacacaa cctaatcaat   1260
agaaaacata tgttttatta aaacaaaatt tatcatatat catatatata tatatatcat   1320
atatatatat aaaccgtagc aatgcacggg catataacta gtgcaactta atacatgtgt   1380
gtattaagat gaataagagg gtatccaaat aaaaaacttg ttgcttacgt atggatcgaa   1440
aggggttgga aacgattaaa cgattaaatc tcttcctagt caaaattgaa tagaaggaga   1500
tttaatatat ccccaatcccc ttcgatcatc caggtgcaac cgtataagtc ctaaagtggt   1560
gaggaacacg aaagaaccat gcattggcat gtaaagctcc aagaatttgt tgtatcctta   1620
acaactcaca gaacatcaac caaaattgca cgtcaagggt attgggtaag aaacaatcaa   1680
acaaatcctc tctgtgtgca aagaaacacg gtgagtcatg ccgagatcat actcatctga   1740
tatacatgct tacagctcac aagacattac aaacaactca tattgcatta caaagatcgt   1800
ttcatgaaaa ataaaatagg ccggacagga caaaaatcct tgacgtgtaa agtaaattta   1860
caacaaaaaa aaagccatat gtcaagctaa atctaattcg ttttacgtag atcaacaacc   1920
tgtagaaggc aacaaaactg agccacgcag aagtacagaa tgattccaga tgaaccatcg   1980
acgtgctacg taaagagagt gacgagtcat atacatttgg caagaaacca tgaagctgcc   2040
tacagccgta tcggtggcat aagaacacaa gaaattgtgt taattaatca aagctataaa   2100
taacgctcgc atgcctgtgc acttctccat caccaccact gggtcttcag accattagct   2160
ttatctactc cagagcgcag aagaacccga tcgacaccat gaagtcggtg gagaagaaac   2220
cgaagggtgt gaagacaggt gcgggtgaca agcataagct gaagacagag tggccggagt   2280
tggtggggaa atcggtggag aaagccaaga aggtgatcct gaaggacaag ccagaggcgc   2340
aaatcatagt tctaccggtt ggtacaaagg tgggtaagca ttataagatc gacaaggtca   2400
agctttttgt ggataaaaag gacaacatcg cgcaggtccc cagggtcggc tagcctcgag   2460
atccccggcg gtgtccccca ctgaagaaac tatgtgctgt agtatagccg ctggctagct   2520
agctagttga gtcatttagc ggcgatgatt gagtaataat gtgtcacgca tcaccatgca   2580
tgggtggcag tctcagtgtg agcaatgacc tgaatgaaca attgaaatga aagaaaaaa   2640
```

```
gtattgttcc aaattaaacg tttttaacctt ttaataggtt tatacaataa ttgatatatg    2700
ttttctgtat atgtctaatt tgttatcatc catttagata tagacgaaaa aaaatctaag    2760
aactaaaaca aatgctaatt tgaaatgaag ggagtatata ttgggataat gtcgatgaga    2820
tccctcgtaa tatcaccgac atcacacgtg tccagttaat gtatcagtga tacgtgtatt    2880
cacatttgtt gcgcgtaggc gtacccaaca attttgatcg actatcagaa agtcaacgga    2940
agcgagtcga cctcgagggg gggcccgtta cccagctttt gttcccttta gtgagggtta    3000
attgcgcgct tggcgtaatc atggtcatag ctgtttcctg tgtgaaattg ttatccgctc    3060
acaattccac acaacatacg agccggaagc ataaagtgta aagcctgggg tgcctaatga    3120
gtgagctaac tcacattaat tgcgttgcgc tcactgcccg ctttccagtc gggaaacctg    3180
tcgtgccagc tgcattaatg aatcggccaa cgcgcgggga gaggcggttt gcgtattggg    3240
cgctcttccg cttcctcgct cactgactcg ctgcgctcgg tcgttcggct gcggcgagcg    3300
gtatcagctc actcaaaggc ggtaatacgg ttatccacag aatcagggga taacgcagga    3360
aagaacatgt gagcaaaagg ccagcaaaag gccaggaacc gtaaaaaggc cgcgttgctg    3420
gcgtttttcc ataggctccg ccccctgac gagcatcaca aaaatcgacg ctcaagtcag    3480
aggtggcgaa acccgacagg actataaaga taccaggcgt ttccccctgg aagctccctc    3540
gtgcgctctc ctgttccgac cctgccgctt accggatacc tgtccgcctt tctcccttcg    3600
ggaagcgtgg cgctttctca tagctcacgc tgtaggtatc tcagttcggt gtaggtcgtt    3660
cgctccaagc tgggctgtgt gcacgaaccc cccgttcagc ccgaccgctg cgccttatcc    3720
ggtaactatc gtcttgagtc aacccggta agacacgact tatcgccact ggcagcagcc    3780
actggtaaca ggattagcag agcgaggtat gtaggcggtg ctacagagtt cttgaagtgg    3840
tggcctaact acggctacac tagaaggaca gtatttggta tctgcgctct gctgaagcca    3900
gttaccttcg aaaaagagt tggtagctct tgatccggca acaaaccac cgctggtagc    3960 ggtggttttt ttgtttgcaa gcagcagatt acgcgcagaa aaaaaggatc tcaagaagat    4020
cctttgatct tttctacggg gtctgacgct cagtggaacg aaaactcacg ttaagggatt    4080
ttggtcatga gattatcaaa aaggatcttc acctagatcc ttttaaatta aaatgaagt    4140 tttaaatcaa tctaaagtat atatgagtaa acttggtctg acagttacca atgcttaatc    4200
agtgaggcac ctatctcagc gatctgtcta tttcgttcat ccatagttgc ctgactcccc    4260
gtcgtgtaga taactacgat acgggagggc ttaccatctg gccccagtgc tgcaatgata    4320
ccgcgagacc cacgctcacc ggctccagat ttatcagcaa taaaccagcc agccggaagg    4380
gccgagcgca gaagtggtcc tgcaacttta tccgcctcca tccagtctat taattgttgc    4440
cgggaagcta gagtaagtag ttcgccagtt aatagtttgc gcaacgttgt tgccattgct    4500
acaggcatcg tggtgtcacg ctcgtcgttt ggtatggctt cattcagctc cggttcccaa    4560
cgatcaaggc gagttacatg atcccccatg ttgtgcaaaa aagcggttag ctccttcggt    4620
cctccgatcg ttgtcagaag taagttggcc gcagtgttat cactcatggt tatggcagca    4680
ctgcataatt ctcttactgt catgccatcc gtaagatgct tttctgtgac tggtgagtac    4740
tcaaccaagt cattctgaga atagtgtatg cggcgaccga gttgctcttg cccggcgtca    4800
atacgggata taccgcgcc acatagcaga actttaaaag tgctcatcat ggaaaacgt    4860 tcttcggggc gaaaactctc aaggatctta ccgctgttga gatccagttc gatgtaaccc    4920
actcgtgcac ccaactgatc ttcagcatct tttactttca ccagcgtttc tgggtgagca    4980
aaaacaggaa ggcaaaatgc cgcaaaaaag ggaataaggg cgacacggaa atgttgaata    5040
```

```
ctcatactct tcctttttca atattattga agcatttatc agggttattg tctcatgagc    5100
ggatacatat ttgaatgtat ttagaaaaat aaacaaatag gggttccgcg cacatttccc    5160
cgaaaagtgc cac                                                      5173
```

<210> SEQ ID NO 8
<211> LENGTH: 54
<212> TYPE: DNA
<213> ORGANISM: Artificial Sequence
<220> FEATURE:
<223> OTHER INFORMATION: Primer designed based upon the alpha
      hordothionin sequence from Hordeum vulgare to amplify the gene and
      to introduce a NcoI site at the start (ATG) codon and a BamHI site
      after the stop codon of the thionin coding sequence to facilitate
      cloning.

<400> SEQUENCE: 8

```
agtataagta aacacaccat cacacccttg aggcccttgc tgtggccat ggtg           54
```

<210> SEQ ID NO 9
<211> LENGTH: 55
<212> TYPE: DNA
<213> ORGANISM: Artificial Sequence
<220> FEATURE:
<223> OTHER INFORMATION: Primer designed based upon the alpha
      hordothionin sequence of Hordeum vulgare to amplify the gene and
      to introduce a NcoI site at the start (ATG) codon and a BamHI site
      after the stop codon of the thionin coding sequence to facilitate
      cloning.

<400> SEQUENCE: 9

```
cctcacatcc cttagtgcct aagttcgacg tcgggccctc tagtcgacgg atcca         55
```

<210> SEQ ID NO 10
<211> LENGTH: 35
<212> TYPE: DNA
<213> ORGANISM: Artificial Sequence
<220> FEATURE:
<223> OTHER INFORMATION: Primer designed for single stranded DNA
      site-directed mutagenesis to introduce into the native Hordeum
      vulgare alpha hordothionin gene 12 codons for lysine, based on the
      peptide structure of hordothionin 12.

<400> SEQUENCE: 10

```
agcggaaaat gcccgaaagg cttccccaaa ttggc                              35
```

<210> SEQ ID NO 11
<211> LENGTH: 45
<212> TYPE: DNA
<213> ORGANISM: Artificial Sequence
<220> FEATURE:
<223> OTHER INFORMATION: Primer designed for single stranded DNA
      site-directed mutagenesis to introduce into the native Hordeum
      vulgare alpha hordothionin gene 12 codons for lysine, based on the
      peptide structure of hordothionin 12.

<400> SEQUENCE: 11

```
tgcgcaggcg tctgcaagtg taagctgact agtagcggaa aatgc                   45
```

<210> SEQ ID NO 12
<211> LENGTH: 50
<212> TYPE: DNA
<213> ORGANISM: Artificial Sequence
<220> FEATURE:
<223> OTHER INFORMATION: Primer designed for single stranded DNA
      site-directed mutagenesis to introduce into the native Hordeum
      vulgare alpha hordothionin gene 12 codons for lysine, based on the
      peptide structure of hordothionin 12.

-continued

```
<400> SEQUENCE: 12
tacaaccttt gcaaagtcaa aggcgccaag aagctttgcg caggcgtctg          50

<210> SEQ ID NO 13
<211> LENGTH: 50
<212> TYPE: DNA
<213> ORGANISM: Artificial Sequence
<220> FEATURE:
<223> OTHER INFORMATION: Primer designed for single stranded DNA
      site-directed mutagenesis to introduce into the native Hordeum
      vulgare alpha hordothionin gene 12 codons for lysine, based on the
      peptide structure of hordothionin 12.

<400> SEQUENCE: 13
gcaagagttg ctgcaagagt accctgggaa ggaagtgcta caaccttttgc         50

<210> SEQ ID NO 14
<211> LENGTH: 609
<212> TYPE: DNA
<213> ORGANISM: Pisum sativum
<220> FEATURE:
<221> NAME/KEY: CDS
<222> LOCATION: (18)...(410)

<400> SEQUENCE: 14
tttctttcta tcaaaca atg gct tcc gtt aaa ctc gct tct ttg atg gtc    50
                Met Ala Ser Val Lys Leu Ala Ser Leu Met Val
                 1               5                  10 ttg ttt gcc aca tta ggt atg ttc ctg aca aaa aac gta gga gca gca   98
Leu Phe Ala Thr Leu Gly Met Phe Leu Thr Lys Asn Val Gly Ala Ala
            15                  20                  25 agc tgc aat ggg gtt tgt tct cca ttt gag atg cca cca tgt ggc tct  146
Ser Cys Asn Gly Val Cys Ser Pro Phe Glu Met Pro Pro Cys Gly Ser
        30                  35                  40 tca gcc tgt cga tgt atc cct gtt ggt cta gtt gtt ggt tac tgc aga  194
Ser Ala Cys Arg Cys Ile Pro Val Gly Leu Val Val Gly Tyr Cys Arg
    45                  50                  55 cat cca tct gga gtt ttc ttg agg acg aat gat gaa cac cct aac tta  242
His Pro Ser Gly Val Phe Leu Arg Thr Asn Asp Glu His Pro Asn Leu
60                  65                  70                  75 tgt gag tct gat gcc gat tgt agg aag aaa gga agt ggt aac ttt tgc  290
Cys Glu Ser Asp Ala Asp Cys Arg Lys Lys Gly Ser Gly Asn Phe Cys
                80                  85                  90 ggt cat tat cct aat cct gat att gaa tat gga tgg tgt ttt gcc tct  338
Gly His Tyr Pro Asn Pro Asp Ile Glu Tyr Gly Trp Cys Phe Ala Ser
            95                  100                 105 aaa tct gaa gca gaa gac ttt ttc tct aag att acc caa aaa gac ttg  386
Lys Ser Glu Ala Glu Asp Phe Phe Ser Lys Ile Thr Gln Lys Asp Leu
        110                 115                 120 ttg aag agt gtt tcc act gct taa tttccatatc cagaacaaaa ccatgcatgc 440
Leu Lys Ser Val Ser Thr Ala
    125                 130 aagacatggt gaagctatct agtactttaa ataaacaaac tttgtttcca acataggagt  500
tggatttcta agatacgcat cacaattcca ataaatgtta tatgtgcatg gttccagtgt  560
tgtaatatat gcagtttctt ttcaaataat aaatcttata tcacaattg              609

<210> SEQ ID NO 15
<211> LENGTH: 130
<212> TYPE: PRT
<213> ORGANISM: Pisum sativum
```

```
<400> SEQUENCE: 15

Met Ala Ser Val Lys Leu Ala Ser Leu Met Val Leu Phe Ala Thr Leu
 1               5                  10                  15

Gly Met Phe Leu Thr Lys Asn Val Gly Ala Ala Ser Cys Asn Gly Val
             20                  25                  30

Cys Ser Pro Phe Glu Met Pro Pro Cys Gly Ser Ser Ala Cys Arg Cys
         35                  40                  45

Ile Pro Val Gly Leu Val Val Gly Tyr Cys Arg His Pro Ser Gly Val
     50                  55                  60

Phe Leu Arg Thr Asn Asp Glu His Pro Asn Leu Cys Glu Ser Asp Ala
65                  70                  75                  80

Asp Cys Arg Lys Lys Gly Ser Gly Asn Phe Cys Gly His Tyr Pro Asn
                 85                  90                  95

Pro Asp Ile Glu Tyr Gly Trp Cys Phe Ala Ser Lys Ser Glu Ala Glu
            100                 105                 110

Asp Phe Phe Ser Lys Ile Thr Gln Lys Asp Leu Leu Lys Ser Val Ser
        115                 120                 125

Thr Ala
    130

<210> SEQ ID NO 16
<211> LENGTH: 1240
<212> TYPE: DNA
<213> ORGANISM: Zea mays
<220> FEATURE:
<221> NAME/KEY: CDS
<222> LOCATION: (234)...(776)

<400> SEQUENCE: 16
gaattcattg acaacccttg acatgtaaag ttgattcata tgtataagaa agcttaatga    60
tctatctgta catccaaatc catgtactat gtttccacgt catgcaacgc aacattccaa   120
aaccatggat catctataaa tggctagctc ccacatatga actagtctct atcatcatcc   180
aatccagatc agcaaagcgg cagtgcgtag agaggatcgt cgaacagaac agc atg     236
                                                              Met
                                                              1 aag atg gtc atc gtt ctc gtc gtg tgc ctg gct ctg tca gct gcc tgc    284
Lys Met Val Ile Val Leu Val Val Cys Leu Ala Leu Ser Ala Ala Cys
            5                  10                  15 gcc tct gca atg cag atg ccc tgc ccc tgc gcg ggg ctg cag ggc ttg    332
Ala Ser Ala Met Gln Met Pro Cys Pro Cys Ala Gly Leu Gln Gly Leu
            20                  25                  30 tac ggc gct ggc gcc ggc ctg acg acg atg atg ggc gcc ggc ggg ctg    380
Tyr Gly Ala Gly Ala Gly Leu Thr Thr Met Met Gly Ala Gly Gly Leu
     35                  40                  45 tac ccc tac gcg gag tac ctg agg cag ccg cag tgc agc ccg ctg gcg    428
Tyr Pro Tyr Ala Glu Tyr Leu Arg Gln Pro Gln Cys Ser Pro Leu Ala
 50                  55                  60                  65 gcg gcg ccc tac tac gcc ggg tgt ggg cag acg agc gcc atg tac cag    476
Ala Ala Pro Tyr Tyr Ala Gly Cys Gly Gln Thr Ser Ala Met Tyr Gln
             70                  75                  80 ccg ctc cgg caa cag tgc tgc cag cag cag atg agg atg atg gac gtg    524
Pro Leu Arg Gln Gln Cys Cys Gln Gln Gln Met Arg Met Met Asp Val
            85                  90                  95 cag tcc gtc gcg cag cag ctg cag atg atg atg cag ctt gag cgt gcc    572
Gln Ser Val Ala Gln Gln Leu Gln Met Met Met Gln Leu Glu Arg Ala
            100                 105                 110
```

```
gct gcc gcc agc agc agc ctg tac gag cca gct ctg atg cag cag cag      620
Ala Ala Ala Ser Ser Ser Leu Tyr Glu Pro Ala Leu Met Gln Gln Gln
    115                 120                 125 cag cag ctg ctg gca gtc cag ggt ctc aac ccc atg gcc atg atg atg      668
Gln Gln Leu Leu Ala Val Gln Gly Leu Asn Pro Met Ala Met Met Met
130                 135                 140                 145 gcg cag aac atg ccg gcc atg ggt gga ctc tac cag tac cag tac cag      716
Ala Gln Asn Met Pro Ala Met Gly Gly Leu Tyr Gln Tyr Gln Tyr Gln
                150                 155                 160 ctg ccc agc tac cgc acc aac ccc tgt ggc gtc tcc gct gcc att ccg      764
Leu Pro Ser Tyr Arg Thr Asn Pro Cys Gly Val Ser Ala Ala Ile Pro
            165                 170                 175 ccc tac tac tga ttcatgatat ttgggaaatc tcctctatcc atccctctct          816
Pro Tyr Tyr
        180 atctatatat gtaataatgc agtaagacga cacacattat catgtgtggt atgaccaata    876 atatatgcat cataataaag ttttggtttt aaagaattat cggacgcttg atatctatga    936 tgctggataa atcaaaactt ctcatataaa ttgtaaatat ttcaaaatct ctatttaggc    996 tccaatggag agcatatggg tagagtagta tatatgcttg aaatactaac aactagcaaa    1056 gtgcgggcac gttgctacat gctcatttat gctcgagcat ggagtataaa acataaagat    1116 atatatgttc cattggcctg gtaaacgctg gatataggtt taaagccaac aactcatggt    1176 tcgaatcccc atttatatat aatccataat tttagcgctt tttaccattt aaattttgga    1236 gtaa                                                                1240

<210> SEQ ID NO 17
<211> LENGTH: 180
<212> TYPE: PRT
<213> ORGANISM: Zea mays

<400> SEQUENCE: 17

Met Lys Met Val Ile Val Leu Val Val Cys Leu Ala Leu Ser Ala Ala
1               5                   10                  15

Cys Ala Ser Ala Met Gln Met Pro Cys Pro Cys Ala Gly Leu Gln Gly
            20                  25                  30

Leu Tyr Gly Ala Gly Ala Gly Leu Thr Thr Met Met Gly Ala Gly Gly
        35                  40                  45

Leu Tyr Pro Tyr Ala Glu Tyr Leu Arg Gln Pro Gln Cys Ser Pro Leu
    50                  55                  60

Ala Ala Ala Pro Tyr Tyr Ala Gly Cys Gly Gln Thr Ser Ala Met Tyr
65                  70                  75                  80

Gln Pro Leu Arg Gln Gln Cys Cys Gln Gln Gln Met Arg Met Met Asp
                85                  90                  95

Val Gln Ser Val Ala Gln Gln Leu Gln Met Met Met Gln Leu Glu Arg
            100                 105                 110

Ala Ala Ala Ser Ser Ser Leu Tyr Glu Pro Ala Leu Met Gln Gln
        115                 120                 125

Gln Gln Gln Leu Leu Ala Val Gln Gly Leu Asn Pro Met Ala Met Met
    130                 135                 140

Met Ala Gln Asn Met Pro Ala Met Gly Gly Leu Tyr Gln Tyr Gln Tyr
145                 150                 155                 160

Gln Leu Pro Ser Tyr Arg Thr Asn Pro Cys Gly Val Ser Ala Ala Ile
                165                 170                 175

Pro Pro Tyr Tyr
        180
```

-continued

<210> SEQ ID NO 18
<211> LENGTH: 2562
<212> TYPE: DNA
<213> ORGANISM: Zea mays
<220> FEATURE:
<221> NAME/KEY: CDS
<222> LOCATION: (1137)...(1589)

<400> SEQUENCE: 18

```
aagcttgcta ctttctttcc ttaatgttga tttccccttt gttagatgtt ctttgtgtta      60
tatacactct gtatacaagg atgcgataca cacatcagct agtcctaatg atgccaccga     120
ctttacttga ggaaaaggaa acaaatatga tgtggccatc acattctcaa taacaatgac     180
catgtgcgca atgacatacc atcatatttg atatcataaa ataaattta ttatcaaagt     240 aaacatatag ttcatatatc agatattaaa gtgataagaa caaatattac attttatctt     300
atataaaatg acgaaaagg tacgagttga aaaggagtcc aaccccttt ttatagcttg      360 ttcggttgct tgttctcttc ggctagcgag gtggtagaat gtgagagtgt tgcgcgtgga     420
ttcccgtcgt agtgttctta ggtgatttct cacggcccat ctgtgatata gcgactcata     480
tgtggtgtaa tagcccattg ggagaagggg agagatatag atctacgtga tttgcacgtg     540
atgcacgacg aacgaaactg gtggtttaaa gtagtagagg tttgtcatta gaggtgtaaa     600
tggtacatat attatccgtt catattcgaa tttgatccgt ataagagggc taagatctaa     660
tccgtataca agtccaagta ttaagtatcc gatccatatc ggatctttat ccgtatccgt     720
atactcaaaa tttgatgttt aagattttaa tatatattta aactttatag gaactcgata     780
atatttgtat ctgatttgaa ttatgaaaac aaatatggaa cgattaattt cagtctatat     840
ccgttccgat atttgtcatg ctttgctaaa ataccttta caaggcatct tgtgcagatt     900
atatattaat ctgaaatcag ttagagaagc ctacaaattt gaccaaatgc cgagtcatcc     960
ggcttatccc ctttccaact ttcagttctg caagcgccag aaatcgtttt tcatctacat    1020
tgtctttgtt gcctgcatac atctataaat aggacctgct agatcaatcg cagtccatcg    1080
gcctcagtcg cacatatcta ctatactata ctctaggaag caaggacacc accgcc atg   1139
                                                                 Met
                                                                  1 gca gcc aag atg ctt gca ttg ttc gct ctc cta gct ctt tgt gca agc    1187
Ala Ala Lys Met Leu Ala Leu Phe Ala Leu Leu Ala Leu Cys Ala Ser
        5                  10                  15 gcc act agt gcg acc cat att cca ggg cac ttg cca cca gtc atg cca    1235
Ala Thr Ser Ala Thr His Ile Pro Gly His Leu Pro Pro Val Met Pro
 20                  25                  30 ttg ggt acc atg aac cca tgc atg cag tac tgc atg atg caa cag ggg    1283
Leu Gly Thr Met Asn Pro Cys Met Gln Tyr Cys Met Met Gln Gln Gly
         35                  40                  45 ctt gcc agc ttg atg gcg tgt ccg tcc ctg atg ctg cag caa ctg ttg    1331
Leu Ala Ser Leu Met Ala Cys Pro Ser Leu Met Leu Gln Gln Leu Leu
 50                  55                  60                  65 gcc tta ccg ctt cag acg atg cca gtg atg atg cca cag atg atg acg    1379
Ala Leu Pro Leu Gln Thr Met Pro Val Met Met Pro Gln Met Met Thr
             70                  75                  80 cct aac atg atg tca cca ttg atg atg ccg agc atg atg tca cca atg    1427
Pro Asn Met Met Ser Pro Leu Met Met Pro Ser Met Met Ser Pro Met
         85                  90                  95 gtc ttg ccg agc atg atg tcg caa ata atg atg cca caa tgt cac tgc    1475
Val Leu Pro Ser Met Met Ser Gln Ile Met Met Pro Gln Cys His Cys
100                 105                 110
```

```
gac gcc gtc tcg cag att atg ctg caa cag cag tta cca ttc atg ttc      1523
Asp Ala Val Ser Gln Ile Met Leu Gln Gln Gln Leu Pro Phe Met Phe
    115                 120                 125 aac cca atg gcc atg acg att cca ccc atg ttc tta cag caa ccc ttt      1571
Asn Pro Met Ala Met Thr Ile Pro Pro Met Phe Leu Gln Gln Pro Phe
130                 135                 140                 145 gtt ggt gct gca ttc tag atagaaatat ttgtgttgta tcgaataatg             1619
Val Gly Ala Ala Phe
                150 agttgacatg ccatcgcgtg tgactcatta ttaacaataa aacaagtttc ctcttattat    1679
cttttatat ctctccctat ccattttgc aaagcccatt atcctttact ccctaagtcc      1739
caatatattt tagaccttaa attgtatgtc tatattcaaa agaatgacaa taaatctaga    1799
catatatata aaacacatac attaagtatt gtatgaatct attaaaatgc taaaacgact    1859
aatattatgg gacggaggga gtactttatt agtagattac attgttattt tctctattcc    1919
aaatataagt ctggtttttc aatcaatcaa tatatattac catgtccaaa cattttgaat    1979
tatatatcta ggtgcagcat ccgtgcacga tcgtaaaaga agcagtcacg gtgttggtcc    2039
caaaaactaa tcgtccgttg tcggtcacct ataaagattc atgaagagaa ccaaaataag    2099
gcaatataat taatgtaata tgactcctcc ttttgaatta cttaggaata acataagcaa    2159
acaaaaaaag gagaagatca aggtaaataa aggcattttg tgagaaaaca tggaagcata    2219
agaatgcata agtaatgatt tgtgtctctt tatatttttt ttattcacgt gaatttacat    2279
agataccatc ggatgttcga tggtaataca atgatgcctt agctccgaga gcttcgaatg    2339
atgagcgatt taaaaatact cctatcaatt gttcgaaagt tctttgtctc atgcatgggc    2399
aatgtacctc tatttatagg gacggtgcga cgtacaaatt tgtataaaat tatatttttta   2459
ttcccaaatc ctatgcatat gtgtcgggga ccataattag gggtaccctc aaggctccta    2519
attctcagct ggtaaccccca tcagcataaa gctgcaaagg cct                     2562
```

<210> SEQ ID NO 19
<211> LENGTH: 150
<212> TYPE: PRT
<213> ORGANISM: Zea mays

<400> SEQUENCE: 19

```
Met Ala Ala Lys Met Leu Ala Leu Phe Ala Leu Leu Ala Leu Cys Ala
 1               5                  10                  15

Ser Ala Thr Ser Ala Thr His Ile Pro Gly His Leu Pro Val Met
            20                  25                  30

Pro Leu Gly Thr Met Asn Pro Cys Met Gln Tyr Cys Met Met Gln Gln
        35                  40                  45

Gly Leu Ala Ser Leu Met Ala Cys Pro Ser Leu Met Leu Gln Gln Leu
    50                  55                  60

Leu Ala Leu Pro Leu Gln Thr Met Pro Val Met Met Pro Gln Met Met
65                  70                  75                  80

Thr Pro Asn Met Met Ser Pro Leu Met Met Pro Ser Met Met Ser Pro
                85                  90                  95

Met Val Leu Pro Ser Met Met Ser Gln Ile Met Met Pro Gln Cys His
            100                 105                 110

Cys Asp Ala Val Ser Gln Ile Met Leu Gln Gln Gln Leu Pro Phe Met
        115                 120                 125
```

```
Phe Asn Pro Met Ala Met Thr Ile Pro Pro Met Phe Leu Gln Gln Pro
    130                 135                 140
Phe Val Gly Ala Ala Phe
145                 150

<210> SEQ ID NO 20
<211> LENGTH: 562
<212> TYPE: DNA
<213> ORGANISM: Oryza sativa
<220> FEATURE:
<221> NAME/KEY: CDS
<222> LOCATION: (51)...(455)

<400> SEQUENCE: 20
cgtctacacc atctggaatc ttgtttaaca ctagtattgt agaatcagca atg gca         56
                                                        Met Ala
                                                          1 gca tac acc agc aag atc ttt gcc ctg ttt gcc tta att gct ctt tct      104
Ala Tyr Thr Ser Lys Ile Phe Ala Leu Phe Ala Leu Ile Ala Leu Ser
        5                   10                  15 gca agt gcc act act gca atc acc act atg cag tat ttc cca cca aca      152
Ala Ser Ala Thr Thr Ala Ile Thr Thr Met Gln Tyr Phe Pro Pro Thr
 20                  25                  30 tta gcc atg ggc acc atg gat ccg tgt agg cag tac atg atg caa acg      200
Leu Ala Met Gly Thr Met Asp Pro Cys Arg Gln Tyr Met Met Gln Thr
 35                  40                  45                  50 ttg ggc atg ggt agc tcc aca gcc atg ttc atg tcg cag cca atg gcg      248
Leu Gly Met Gly Ser Ser Thr Ala Met Phe Met Ser Gln Pro Met Ala
             55                  60                  65 ctc ctg cag cag caa tgt tgc atg cag cta caa ggc atg atg cct cag      296
Leu Leu Gln Gln Gln Cys Cys Met Gln Leu Gln Gly Met Met Pro Gln
         70                  75                  80 tgc cac tgt ggc acc agt tgc cag atg atg cag agc atg caa caa gtt      344
Cys His Cys Gly Thr Ser Cys Gln Met Met Gln Ser Met Gln Gln Val
     85                  90                  95 att tgt gct gga ctc ggg cag cag cag atg atg aag atg gcg atg cag      392
Ile Cys Ala Gly Leu Gly Gln Gln Gln Met Met Lys Met Ala Met Gln
100                 105                 110 atg cca tac atg tgc aac atg gcc cct gtc aac ttc caa ctc tct tcc      440
Met Pro Tyr Met Cys Asn Met Ala Pro Val Asn Phe Gln Leu Ser Ser
115                 120                 125                 130 tgt ggt tgt tgt tga tcaaacgttg gttacatgta ctctagtaat aaggtgttgc      495
Cys Gly Cys Cys atactatcgt gtgcaaacac tagaaataag aaccattgaa taaaatatca atcattttca    555
gacttgc                                                              562

<210> SEQ ID NO 21
<211> LENGTH: 134
<212> TYPE: PRT
<213> ORGANISM: Oryza sativa

<400> SEQUENCE: 21

Met Ala Ala Tyr Thr Ser Lys Ile Phe Ala Leu Phe Ala Leu Ile Ala
  1               5                  10                  15

Leu Ser Ala Ser Ala Thr Thr Ala Ile Thr Thr Met Gln Tyr Phe Pro
             20                  25                  30

Pro Thr Leu Ala Met Gly Thr Met Asp Pro Cys Arg Gln Tyr Met Met
         35                  40                  45

Gln Thr Leu Gly Met Gly Ser Ser Thr Ala Met Phe Met Ser Gln Pro
     50                  55                  60
```

-continued

```
Met Ala Leu Leu Gln Gln Gln Cys Cys Met Gln Leu Gln Gly Met Met
 65                  70                  75                  80

Pro Gln Cys His Cys Gly Thr Ser Cys Gln Met Met Gln Ser Met Gln
                 85                  90                  95

Gln Val Ile Cys Ala Gly Leu Gly Gln Gln Gln Met Met Lys Met Ala
            100                 105                 110

Met Gln Met Pro Tyr Met Cys Asn Met Ala Pro Val Asn Phe Gln Leu
        115                 120                 125

Ser Ser Cys Gly Cys Cys
    130

<210> SEQ ID NO 22
<211> LENGTH: 45
<212> TYPE: PRT
<213> ORGANISM: Triticum aestivum

<400> SEQUENCE: 22

Lys Ser Cys Cys Lys Ser Thr Leu Gly Arg Asn Cys Tyr Asn Leu Cys
 1               5                  10                  15

Arg Ala Arg Gly Ala Gln Lys Leu Cys Ala Asn Val Cys Arg Cys Lys
            20                  25                  30

Leu Thr Ser Gly Leu Ser Cys Pro Lys Asp Phe Pro Lys
         35                  40                  45
```

ALTERATION OF AMINO ACID COMPOSITIONS IN SEEDS

BACKGROUND OF THE INVENTION

Feed formulations based on crop plants must typically be supplemented with specific amino acids to provide animals with essential nutrients which are necessary for their growth. This supplementation is necessary because, in general, crop plants contain low proportions of several amino acids which are essential for, and cannot be synthesized by, monogastric animals.

The seeds of crop plants contain different classes of seed proteins. The amino acid composition of these seeds reflects the composition of the prevalent classes of proteins. Amino acid limitations are usually due to amino acid deficiencies of these prevalent protein classes.

Among the amino acids necessary for animal nutrition, those that are of limited availability in crop plants include methionine, lysine, and threonine. Attempts to increase the levels of these amino acids by breeding, mutant selection, and/or changing the composition of the storage proteins accumulated in the seeds of crop plants, have met with limited success, or were accompanied by a loss in yield.

For example, although seeds of corn plants containing a mutant transcription factor, (opaque 2), or a mutant α-zein gene, (floury 2), exhibit elevated levels of total and bound lysine, there is an altered seed endosperm structure which is more susceptible to damage and pests. Significant yield losses are also typical.

An alternative means to enhance levels of free amino acids in a crop plant is the modification of amino acid biosynthesis in the plant. The introduction of a feedback-regulation-insensitive dihydrodipicolinic acid synthase ("DHDPS") gene, which encodes an enzyme that catalyzes the first reaction unique to the lysine biosynthetic pathway, into plants has resulted in an increase in the levels of free lysine in the leaves and seeds of those plants. An increase in the levels of free lysine in the embryo results in reduced amount of oil in the seed. Further free lysine can be lost during the wet milling process reducing the feed value of the gluten product of the process.

The expression of the lysC gene, which encodes a mutant bacterial aspartate kinase that is desensitized to feedback inhibition by lysine and threonine, from a seed-specific promoter in tobacco plants, has resulted in an increase in methionine and threonine biosynthesis in the seeds of those plants. See Karchi, et al.; *The Plant J.*; Vol. 3; p. 721; (1993). However, expression of the lysC gene results in only a 6–7% increase in the level of total threonine or methionine in the seed. The expression of the lysC gene in seeds has a minimal impact on the nutritional value of those seeds and, thus, supplementation of feed containing lysC transgenic seeds with amino acids, such as methionine and threonine, is still required.

There are additional molecular genetic strategies available for enhancing the amino acid quality of plant proteins. Each involves molecular manipulation of plant genes and the generation of transgenic plants.

Protein sequence modification involves the identification of a gene encoding a major protein, preferably a storage protein, as the target for modification to contain more codons of essential amino acids. An important aspect of this approach is to be able to select a region of the protein that can be modified without affecting the overall structure, stability, function, and other cellular and nutritional properties of the protein.

The development of DNA synthesis technology allows the design and synthesis of a gene encoding a new protein with desirable essential amino acid compositions. For example, researchers have synthesized a 292-base pair DNA sequence encoding a polypeptide composed of 80% essential amino acids and used it with the nopaline synthetase (NOS) promoter to construct a chimeric gene. Expression of this gene in the tuber of transgenic potato has resulted in an accumulation of this protein at a level of 0.02% to 0.35% of the total plant protein. This low level accumulation is possibly due to the weak NOS promoter and/or the instability of the new protein.

Tobacco has been used as a test plant to demonstrate the feasibility of this approach by transferring a chimeric gene containing the bean phaseolin promoter and the cDNA of a sulfur-rich protein Brazil Nut Protein ("BNP"), (18 mol % methionine and 8 mol % cysteine) into tobacco. Amino acid analysis indicates that the methionine content in the transgenic seeds is enhanced by 30% over that of the untransformed seeds. This same chimeric gene has also been transferred into a commercial crop, canola, and similar levels of enhancement were achieved.

However, an adverse effect is that lysine content decreases. Additionally, BNP has been identified as a major food allergen. Thus it is neither practical nor desirable to use BNP to enhance the nutritional value of crop plants.

Thus, there is a need to improve the nutritional value of plant seeds. The genetic modification should not be accompanied by detrimental side effects such as allergenicity, anti-nutritional quality or poor yield.

SUMMARY OF THE INVENTION

It is an object of the present invention to provide a seed, the endosperm of which contains elevated levels of an essential amino acid.

It is a further object of the present invention to provide methods for increasing the nutritional value of feed.

It is a further object of the present invention to provide methods for genetically modifying seeds so as to increase amounts of essential amino acids which are present in relatively low amounts in unmodified seeds.

It is a further object of the present invention to provide methods for increasing the nutritional content of seeds without detrimental side effects such as allergenicity or anti-nutritional quality.

It is a further object of the present invention to provide methods for increasing the nutritional content of seeds while maintaining a high yield.

It is a further object of the present invention to provide a method for the expression of a polypeptide in a seed having levels of a preselected amino acid sufficient to reduce or obviate feed supplementation.

According to the present invention a transformed plant seed is provided, the endosperm of which is characterized as having an elevated level of at least one preselected amino acid compared to a seed from a corresponding plant which has not been transformed, wherein the amino acid is lysine, threonine, or tryptophan and optionally a sulfur-containing amino acid.

Also provided is a seed from a plant which has been transformed to express a heterologous protein in the endosperm of the seed, wherein the seed exhibits an elevated level of an essential amino acid.

An expression cassette is also provided comprising a seed endosperm-preferred promoter operably linked to a structural gene encoding a polypeptide having an elevated level of a preselected amino acid. Transformed plants and seeds containing the expression cassette are also provided.

A method for elevating the level of a preselected amino acid in the endosperm of plant seed is also provided. The method comprises the transformation of plant cells by introducing the expression cassette, recovering the transformed cells, regenerating a transformed plant and collecting the seeds therefrom.

DETAILED DESCRIPTION OF THE INVENTION

As used herein, a "structural gene" means an exogenous or recombinant DNA sequence or segment that encodes a polypeptide.

As used herein, "recombinant DNA" is a DNA sequence or segment that has been isolated from a cell, purified, synthesized or amplified.

As used herein, "isolated" means either physically isolated from the cell or synthesized in vitro on the basis of the sequence of an isolated DNA segment.

As used herein, the term "increased" or "elevated" levels of the preselected amino acid in a protein means that the protein contains an elevated amount of a preselected amino acid compared to the amount in an average protein.

As used herein, "increased" or "elevated" levels or amounts of preselected amino acids in a transformed plant or seed are levels which are greater than the levels or amounts in the corresponding untransformed plant or seed.

As used herein, "polypeptide" means proteins, protein fragments, modified proteins, amino acid sequences and synthetic amino acid sequences.

As used herein, "transformed plant" means a plant which comprises a structural gene which is introduced into the genome of the plant by transformation.

As used herein, "untransformed plant" refers to a wild type plant, i.e., one where the genome has not been altered by the introduction of the structural gene.

As used herein, "plant" includes but is not limited to plant cells, plant tissue and plant seeds.

As used herein, "seed endosperm-preferred promoter" is a promoter which preferentially promotes expression of the structural gene in the endosperm of the seed.

As used herein with respect to a structural gene encoding a polypeptide, the term "expresses" means that the structural gene is incorporated into the genome of cells, so that the product encoded by the structural gene is produced within the cells.

As used herein, the term "essential amino acid" means an amino acid which is synthesized only by plants or microorganisms or which is not produced by animals in sufficient quantities to support normal growth and development.

As used herein, the term "high lysine content protein" means that the protein has at least about 7 mole % lysine, preferably about 7 mole % to about 50 mole % lysine, more preferably about 7 mole % to about 40 mole % lysine and most preferably about 7 mole % to about 30 mole %.

As used herein, the term "high sulfur content protein" means that the protein contains at least about 6 mole % methionine and/or cysteine, preferably about 6 mole % to about 40 mole %, more preferably about 6 mole % to about 30 mole % and most preferably 6 mole % to 25 mole %.

The present invention provides a transformed plant seed, the endosperm of which is characterized as having an elevated level of a preselected amino acid compared to the seed of a corresponding plant which has not been transformed. It is preferred that the level of preselected amino acid is elevated in the endosperm in preference to other parts of the seed.

The preselected amino acid is an essential amino acid such as lysine, cysteine, methionine, threonine, tryptophan, arginine, valine, leucine, isoleucine, histidine or combinations thereof, preferably, the preselected amino acid is lysine, threonine, cysteine, tryptophan, or combinations thereof and optionally methionine. It is especially preferred that the polypeptide has an increased content of lysine as well as a sulfur containing amino acid, i.e., methionine and/or cysteine.

The polypeptide can be an endogenous or heterologous protein. When an endogenous protein is expressed, the preselected amino acid is lysine, cysteine, threonine, tryptophan, arginine, valine, leucine, isoleucine, histidine or combinations thereof and optionally methionine. When the protein is a heterologous protein, any of the above described preselected amino acids or combinations thereof is present in elevated amounts.

Generally the amount of preselected amino acid in the seed of the present invention is at least about 10 percent by weight greater than in a corresponding untransformed seed, preferably about 10 percent by weight to about 10 times greater, more preferably about 15 percent by weight to about 10 time greater and most preferably about 20 percent to about 10 times greater.

A polypeptide having an elevated amount of the preselected amino acid is expressed in the transformed plant seed endosperm in an amount sufficient to increase the amount of at least one preselected amino acid in the seed of the transformed plant, relative to the amount of the preselected amino acid in the seed of a corresponding untransformed plant.

The choice of the structural gene is based on the desired amino acid composition of the polypeptide encoded by the structural gene, and the ability of the polypeptide to accumulate in seeds. The amino acid composition of the polypeptide can be manipulated by methods, such as site-directed mutagenesis of the structural gene encoding the polypeptide, so as to result in expression of a polypeptide that is increased in the amount of a particular amino acid. For example, site-directed mutagenesis can be used to increase levels of lysine, methionine, cysteine, threonine and/or tryptophan and/or to decrease levels of asparagine and/or glutamine.

The derivatives differ from the wild-type protein by one or more amino acid substitutions, insertions, deletions or the like. Typically, amino acid substitutions are conservative. In the regions of homology to the native sequence, variants preferably have at least 90% amino acid sequence identity, more preferably at least 95% identity.

Typical examples of suitable proteins include barley chymotrypsin inhibitor, barley alpha hordothionin, soybean 2S albumin proteins, rice high methionine and rice high methionine proteins and derivatives of each protein.

Barley alpha hordothionin has been modified to increase the level of particular amino acids. The sequences of genes which express modified alpha hordothionin proteins with enhanced essential amino acids are based on the mRNA sequence of the native *Hordeum vulgare* alpha hordothionin gene (accession number X05901, Ponz et al. 1986 *Eur. J. Biochem.* 156:131–135).

Modified hordothionin proteins are described in U.S. Pat. No. 5,990,389 issued Nov. 23, 1999; U.S. Pat. No. 5,885,801 issued Mar. 23, 1999. U.S. Pat. No. 5,885,802 issued Mar.

23, 1999; and U.S. Pat. No. 5,703,409 issued Dec. 30, 1997 the disclosures of which are incorporated herein in their entirety by reference.

Alpha hordothionin is a 45-amino acid protein which is stabilized by four disulfide bonds resulting from eight cysteine residues. In its native form, the protein is especially rich in arginine and lysine residues, containing 5 residues (10%) of each. However, it is devoid of the essential amino acid methionine.

Alpha hordothionin has been modified to increase the amount of various amino acids such as lysine, threonine or methionine. The protein has been synthesized and the three-dimensional structure determined by computer modeling. The modeling of the protein predicts that the ten charged residues (arginine at positions 5, 10, 17, 19 and 30, and lysine at positions 1, 23, 32, 38 and 45) all occur on the surface of the molecule. The side chains of the polar amino acids (asparagine at position 11, glutamine at position 22 and threonine at position 41) also occur on the surface of the molecule. Furthermore, the hydrophobic amino acids, (such as the side chains of leucine at positions 8, 15, 24 and 33 and valine at position 18) are also solvent-accessible.

The Three-dimensional modeling of the protein indicates that the arginine residue at position 10 is important to retention of the appropriate 3-dimensional structure and possible folding through hydrogen bond interactions with the C-terminal residue of the protein. A lysine, methionine or threonine substitution at that point would disrupt this hydrogen bonding network, leading to a destabilization of the structure. The synthetic peptide having this substitution could not be made to fold correctly, which supported this analysis. Conservation of the arginine residue at position 10 provides a protein which folds correctly.

Alpha hordothionin has been modified to contain 12 lysine residues in the mature hordothionin peptide, referred to as HT12. (Rao et al. 1994 Protein Engineering 7(12): 1485–1493 and WO 94/16078 published Jul. 21, 1994, now U.S. Pat. No. 5,990,389 issued Nov. 23, 1999). The disclosure of each of these is incorporated herein by reference in their entirety.

Further analysis of substitutions which would not alter the 3-dimensional structure of the molecule led to replacement of Asparagine-11, Glutamine-22 and Threonine-41 with lysine residues with virtually no steric hindrance. The resulting compound contains 27% lysine residues.

Other combinations of these substitutions were also made, including changes in amino acid residues at one or more of positions 5, 11, 17, 19, 22, 30 and 41 are lysines, and the remainder of the residues at those positions are the residues at the corresponding positions in the wild type hordothionin.

Since threonine is a polar amino acid, the surface polar amino acid residues, asparagine at position 11 and glutamine at position 22, can be substituted; and the charged amino acids, lysine at positions 1, 23, 32 and 38 and arginine at positions 5, 17, 19, and 30, can also be substituted with threonine. The molecule can be synthesized by solid phase peptide synthesis.

While the above sequence is illustrative of the present invention, it is not intended to be a limitation. Threonine substitutions can also be performed at positions containing charged amino acids. Only arginine at position 10 and lysine at position 45 are important for maintaining the structure of the protein. One can also substitute at the sites having hydrophobic amino acids. These include positions 8, 15, 18 and 24.

Since methionine is a hydrophobic amino acid, the surface hydrophobic amino acid residues, leucine at positions 8, 15, and 33, and valine at position 18, were substituted with methionine. The surface polar amino acids, asparagine at position 11, glutamine at position 22 and threonine at position 41, are substituted with methionine. The molecule is synthesized by solid phase peptide synthesis and folds into a stable structure. It has seven methionine residues (15.5%) and, including the eight cysteines, the modified protein has a sulfur amino acid content of 33%.

While the above-described proteins are illustrative of suitable polypeptides which can be expressed in the transformed plant, it is not intended to be a limitation. Methionine substitutions can also be performed at positions containing charged amino acids. Only arginine at position 10 is important for maintaining the structure of the protein through a hydrogen-bonding network with serine at position 2 and lysine at position 45. Thus, one can substitute methionine for lysine at positions 1, 23, 32, and/or 38, and for arginine at positions 5, 17, 19 and/or 30.

Many other proteins are also appropriate, for example the protein encoded by the structural gene can be a lysine and/or sulfur rich seed protein, such as the soybean 2S albumin described in U.S. Pat. No. 5,850,016 issued Dec. 15, 1998, and the chymotrypsin inhibitor from barley, Williamson et al., *Eur. J Biochem* 165:99–106 (1987), the disclosures of each are incorporated by reference.

Derivatives of these genes can be made by site directed mutagenesis to increase the level of preselected amino acids in the encoded polypeptide. For example the gene encoding for the barley high lysine polypeptide (BHL), is derived from barley chymotrypsin inhibitor, WO 98/20133 published May 14, 1998, the disclosures of which is incorporated herein by reference. The gene encoding for the enhanced soybean albumin gene (ESA), is derived from soybean 2S albumin described in U.S. Pat. No. 5,850,016, the disclosure of which is incorporated herein in its entirety by reference.

Other examples of sulfur-rich plant proteins within the scope of the invention include plant proteins enriched in cysteine but not methionine, such as the wheat endosperm purothionine (Mak and Jones; *Can. J. Biochem.*; Vol. 22; p. 83J; (1976) SEQ ID NO: 22; incorporated herein in its entirety by reference), the pea low molecular weight albumins (Higgins, et al.; *J. Biol. Chem.*; Vol. 261; p. 11124; (1986) SEQ ID NO: 14–15; incorporated herein in its entirety by reference) as well as 2S albumin genes from other organisms. See, for example, Coulter, et al.; *J. Exp. Bot.*; Vol. 41; p. 1541; (1990); incorporated herein in its entirety by reference.

Such proteins also include methionine-rich plant proteins (Lilley, et al.; In: *Proceedings of the World Congress on Vegetable Protein Utilization in Human Foods and Animal Feedstuffs*; Applewhite, H. (ed.); American Oil Chemists Soc.; Champaign, Ill.; pp. 497–502; (1989); incorporated herein in its entirety by reference), corn (Pedersen, et al.; *J. Biol. Chem.* p. 261; p. 6279; (1986) SEQ ID NOS: 16–17; Kirihara, et al.; *Gene*, Vol. 71; p. 359; (1988) SEQ ID NOS: 18–19; both incorporated herein in its entirety by reference), and rice (Musumura, et al.; *Plant Mol. Biol.*; Vol. 12; p. 123; (1989) SEQ ID NOS: 20–21; incorporated herein in its entirety by reference).

The present invention also provides a method for genetically modifying plants to increase the level of at least one preselected amino acid in the endosperm of the seed so as to enhance the nutritional value of the seeds.

The method comprises the introduction of an expression cassette into regenerable plant cells to yield transformed plant cells. The expression cassette comprises a seed endosperm-preferred promoter operably linked to a structural gene encoding a polypeptide elevated in content of the preselected amino acid.

A fertile transformed plant is regenerated from the transformed cells, and seeds are isolated from the plant. The structural gene is transmitted through a complete normal sexual cycle of the transformed plant to the next generation.

The polypeptide is synthesized in the endosperm of seed of the plant which has been transformed by insertion of the expression cassette described above. The sequence for the nucleotide molecule, either RNA or DNA, can readily be derived from the amino acid sequence for the selected polypeptide using standard reference texts.

Plants which can be used in the method of the invention include monocotyledonous cereal plants. Preferred plants include maize, wheat, rice, barley, oats, sorghum, millet and rye. The most preferred plant is maize.

Seeds derived from plants regenerated from transformed plant cells, plant parts or plant tissues, or progeny derived from the regenerated transformed plants, may be used directly as feed or food, or further processing may occur.

Transformation

The transformation of plants in accordance with the invention may be carried out in essentially any of the various ways known to those skilled in the art of plant molecular biology. These include, but are not limited to, microprojectile bombardment, microinjection, electroporation of protoplasts or cells comprising partial cell walls, and *Agrobacterium*-mediated DNA transfer.

1. DNA Used for Transformation

DNA useful for introduction into plant cells includes DNA that has been derived or isolated from any source, that may be subsequently characterized as to structure, size and/or function, chemically altered, and later introduced into the plant.

An example of DNA "derived" from a source, would be a DNA sequence or segment that is identified as a useful fragment within a given organism, and which is then synthesized in essentially pure form. An example of such DNA "isolated" from a source would be a useful DNA sequence that is excised or removed from the source by chemical means, e.g., by the use of restriction endonucleases, so that it can be further manipulated, e.g., amplified, for use in the invention, by the methodology of genetic engineering.

Therefore, useful DNA includes completely synthetic DNA, semi-synthetic DNA, DNA isolated from biological sources, and DNA derived from RNA. The DNA isolated from biological sources, or DNA derived from RNA, includes, but is not limited to, DNA or RNA from plant genes, and non-plant genes such as those from bacteria, yeasts, animals or viruses. The DNA or RNA can include modified genes, portions of genes, or chimeric genes, including genes from the same or different genotype.

The term "chimeric gene" or "chimeric DNA" is defined as a gene or DNA sequence or segment comprising at least two DNA sequences or segments from species which do not recombine DNA under natural conditions, or which DNA sequences or segments are positioned or linked in a manner which does not normally occur in the native genome of untransformed plant.

A structural gene of the invention can be identified by standard methods, e.g., enrichment protocols, or probes, directed to the isolation of particular nucleotide or amino acid sequences. The structural gene can be identified by obtaining and/or screening of a DNA or cDNA library generated from nucleic acid derived from a particular cell type, cell line, primary cells, or tissue.

Screening for DNA fragments that encode all or a portion of the structural gene can be accomplished by screening plaques from a genomic or cDNA library for hybridization to a probe of the structural gene from other organisms or by screening plaques from a cDNA expression library for binding to antibodies that specifically recognize the polypeptide encoded by the structural gene.

DNA fragments that hybridize to a structural gene probe from other organisms and/or plaques carrying DNA fragments that are immunoreactive with antibodies to the polypeptide encoded by the structural gene can be subcloned into a vector and sequenced and/or used as probes to identify other cDNA or genomic sequences encoding all or a portion of the structural gene.

Portions of the genomic copy or copies of the structural gene can be partially sequenced and identified by standard methods including either DNA sequence homology to other homologous genes or by comparison of encoded amino acid sequences to known polypeptide sequences.

Once portions of the structural gene are identified, complete copies of the structural gene can be obtained by standard methods, including cloning or polymerase chain reaction (PCR) synthesis using oligonucleotide primers complementary to the structural gene. The presence of an isolated full-length copy of the structural gene can be verified by comparison of its deduced amino acid sequence with the amino acid sequence of native polypeptide sequences.

As discussed above, the structural gene encoding the polypeptide can be modified to increase the content of particular amino acid residues in that polypeptide by methods well known to the art, including, but not limited to, site-directed mutagenesis. Thus, derivatives of naturally occurring polypeptides can be made by nucleotide substitution of the structural gene so as to result in a polypeptide having a different amino acid at the position in the polypeptide which corresponds to the codon with the nucleotide substitution. The introduction of multiple amino acid changes in a polypeptide can result in a polypeptide which is significantly enriched in a preselected amino acid.

As noted above, the choice of the polypeptide encoded by the structural gene will be based on the amino acid composition of the polypeptide and its ability to accumulate in seeds. The amino acid can be chosen for its nutritional value to produce a value-added trait to the plant or plant part. Amino acids desirable for value-added traits, as well as a source to limit synthesis of an endogenous protein include, but are not limited to, lysine, threonine, tryptophan, methionine, and cysteine.

Expression Cassettes and Expression Vectors

According to the present invention, a structural gene is identified, isolated, and combined with a seed endosperm-preferred promoter to provide a recombinant expression cassette.

The construction of such expression cassettes which can be employed in conjunction with the present invention are well known to those of skill in the art in light of the present disclosure. See, e.g., Sambrook, et al.; *Molecular Cloning: A Laboratory Manual*; Cold Spring Harbor, N.Y.; (1989); Gelvin, et al.; *Plant Molecular Biology Manual*; (1990); *Plant Biotechnology: Commercial Prospects and Problems*, eds Prakash, et al.; Oxford & IBH Publishing Co.; New Delhi, India; (1993); and Heslot, et al.; *Molecular Biology and Genetic Engineering of Yeasts*; CRC Press, Inc., USA; (1992); each incorporated herein in its entirety by reference.

Preferred promoters useful in the practice of the invention are those seed endosperm-preferred promoters that allow expression of the structural gene selectively in seed endosperm to avoid any potential deleterious effects associated with the expression of the structural gene in the embryo.

It has been found that when endosperm-preferred promoters are employed, the total level of the preselected amino acid in the seed is increased compared to a seed produced by employing an embryo-preferred promoter, such as the globulin1 promoter. When the globulin1 promoter is employed, the polypeptide is expressed by the structural gene, but the total amount of the preselected amino acid is not increased.

Examples of suitable promoters include, but are not limited to, 27 kD gamma zein promoter and waxy promoter. See the following sites relating to the 27 kD gamma zein promoter: Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18 (21), 6426 (1990). See the following site relating to the waxy promoter: Kloesgen, R. B., Gierl, A., Schwarz-Sommer, Z S. and Saedler, H., Molecular analysis of the waxy locus of *Zea mays, Mol. Gen. Genet.* 203, 237–244 (1986). The disclosures each of these are incorporated herein by reference in their entirety.

However, other endosperm-preferred promoters can be employed.

II. Delivery of DNA to Cells

The expression cassette or vector can be introduced into prokaryotic or eukaryotic cells by currently available methods which are described in the literature. See for example, Weising et al., *Ann. Rev. Genet.* 2: 421–477 (1988). For example, the expression cassette or vector can be introduced into plant cells by methods including, but not limited to, *Agrobacterium*-mediated transformation, electroporation, PEG poration, microprojectile bombardment, microinjection of plant cell protoplasts or embryogenic callus, silicon fiber delivery, infectious viruses or viroids such as retroviruses, the use of liposomes and the like, all in accordance with well-known procedures.

The introduction of DNA constructs using polyethylene glycol precipitation is described in Paszkowski et al., *Embo J.* 3: 2717–2722 (1984). Electroporation techniques are described in Fromm et al., *Proc. Natl. Acad. Sci.* 82: 5324 (1985). Ballistic transformation techniques are described in Klein et al., *Nature* 327: 70–73 (1987). The disclosure of each of these is incorporated herein in its entirety by reference.

Introduction and expression of foreign genes in plants has been shown to be possible using the T-DNA of the tumor-inducing (Ti) plasmid of *Agrobacterium tumefaciens*. Using recombinant DNA techniques and bacterial genetics, a wide variety of foreign DNAs can be inserted into T-DNA in *Agrobacterium*. Following infection by the bacterium containing the recombinant Ti plasmid, the foreign DNA is inserted into the host plant chromosomes, thus producing a genetically engineered cell and eventually a genetically engineered plant. A second approach is to introduce root-inducing (Ri) plasmids as the gene vectors.

*Agrobacterium tumefaciens*-mediated transformation techniques are well described in the literature. See, for example Horsch et al., *Science* 233: 496–498 (1984), and Fraley et al., *Proc. Natl. Acad. Sci.* 80: 4803 (1983). *Agrobacterium* transformation of maize is described in U.S. Pat. No. 5,550,318. The disclosure of each of these is incorporated herein in its entirety by reference.

Other methods of transfection or transformation include (1) *Agrobacterium rhizogenes*-mediated transformation (see, e.g., Lichtenstein and Fuller In: *Genetic Engineering*, vol. 6, PWJ Rigby, Ed., London, Academic Press, 1987; and Lichtenstein, C. P., and Draper, J,. In: *DNA Cloning*, Vol. II, D. M. Glover, Ed., Oxford, IRI Press, 1985). Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25: 1353, 1984), (3) the vortexing method (see, e.g., Kindle, *Proc. Natl. Acad. Sci.*, USA 87: 1228, (1990). The disclosure of each of these is incorporated herein in its entirety by reference.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plane Mol. Biol. Reporter*, 6:165 (1988). The disclosure of each of these is incorporated herein in its entirety by reference.

Expression of polypeptide coding genes can be obtained by injection of the DNA into reproductive organs of a plant as described by Pena et al., *Nature*, 325:274 (1987). The disclosure of which is incorporated herein in its entirety by reference.

DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo* 1986, Butterworth, Stoneham, Mass., pp. 27–54 (1986). The disclosure of each of these is incorporated herein in its entirety by reference.

Plant cells useful for transformation include cells cultured in suspension cultures, callus, embryos, meristem tissue, pollen, and the like.

A variety of plant viruses that can be employed as vectors are known in the art and include cauliflower mosaic virus (CaMV), geminivirus, brome mosaic virus, and tobacco mosaic virus.

Typical vectors useful for expression of genes in higher plants are well known in the art and include vectors derived from the tumor-inducing (Ti) plasmid of *Agrobacterium tumefaciens* described by Rogers et al., *Meth. In Enzymol.*, 153:253–277 (1987). These vectors are plant integrating vectors in that on transformation, the vectors integrate a portion of vector DNA into the genome of the host plant. The disclosure of which is incorporated herein in its entirety by reference.

A particularly preferred vector is a plasmid, by which is meant a circular double-stranded DNA molecule which is not a part of the chromosomes of the cell. Exemplary *A. tumefaciens* vectors useful herein are plasmids pKYLX6 and pKYLX7 of Schardl et al., *Gene*, 61:1–11 (1987) and Berger et al., *Proc. Natl. Acad. Sci. U.S.A.*, 86:8402–8406 (1989). Another useful vector herein is plasmid pBI101.2 that is available from Clontech Laboratories, Inc. (Palo Alto, Calif.). The disclosure of each of these is incorporated herein in its entirety by reference.

A cell in which the foreign genetic material in a vector is functionally expressed has been "transformed" by the vector and is referred to as a "transformant".

Either genomic DNA or cDNA coding the gene of interest may be used in this invention. The gene of interest may also be constructed partially from a cDNA clone and partially from a genomic clone.

When the gene of interest has been isolated, genetic constructs are made which contain the necessary regulatory sequences to provide for efficient expression of the gene in the host cell.

According to this invention, the genetic construct will contain (a) a genetic sequence coding for the polypeptide of interest and (b) one or more regulatory sequences operably linked on either side of the structural gene of interest. Typically, the regulatory sequences will be a promoter or a terminator. The regulatory sequences may be from autologous or heterologous sources.

The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typical selectable markers include genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Genes coding for resistance to herbicides include genes which act to inhibit the action of acetolactate synthase (ALS), in particular the sulfonylurea-type herbicides (e.g., the acetolactate synthase (ALS) genes containing mutations leading to such resistance in particular the S4 and/or Hra mutations), genes coding for resistance to herbicides which act to inhibit action of glutamine synthase, such as phosphinothricin or basta (e.g., the pat or bar gene), or other such genes known in the art. The bar gene encodes resistance to the herbicide basta, and the ALS gene encodes resistance to the herbicide chlorsulfuron.

Typically, an intermediate host cell will be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes, including bacterial hosts such as *E. coli, S. typhimurium*, and *Serratia marcescens*. Eukaryotic hosts such as yeast or filamentous fungi may also be used in this invention. Since these hosts are also microorganisms, it will be essential to ensure that plant promoters which do not cause expression of the polypeptide in bacteria are used in the vector.

The isolated cloning vector will then be introduced into the plant cell using any convenient transformation technique as described above.

III. Regeneration and Analysis of Transformants

Following transformation, regeneration is involved to obtain a whole plant from transformed cells and the presence of structural gene (s) or "transgene(s)" in the regenerated plant is detected by assays. The seed derived from the plant is then tested for levels of preselected amino acids. Depending on the type of plant and the level of gene expression, introduction of the structural gene into the plant seed endosperm can enhance the level of preselected amino acids in an amount useful to supplement the nutritional quality of those seeds.

Using known techniques, protoplasts and cell or tissue culture can be regenerated to form whole fertile plants which carry and express the gene for a polypeptide according to this invention.

Accordingly, a highly preferred embodiment of the present invention is a transformed maize plant, the cells of which contain at least one copy of the DNA sequence of an expression cassette containing a gene encoding a polypeptide containing elevated amounts of an essential amino acid, such an HT12, BHL or ESA protein.

Techniques for regenerating plants from tissue culture, such as transformed protoplasts or callus cell lines, are known in the art. For example, see Phillips, et al.; *Plant Cell Tissue Organ Culture*; Vol. 1; p. 123; (1981); Patterson, et al.; *Plant Sci.*; Vol. 42; p. 125; (1985); Wright, et al.,; *Plant Cell Reports*; Vol. 6; p. 83; (1987); and Barwale, et al.; *Planta*; Vol. 167; p. 473; (1986); each incorporated herein in its entirety by reference. The selection of an appropriate method is within the skill of the art.

Examples of the practice of the present invention detailed herein relate specifically to maize plants. However, the present invention is also applicable to other cereal plants. The expression vectors utilized herein are demonstrably capable of operation in cells of cereal plants both in tissue culture and in whole plants. The invention disclosed herein is thus operable in monocotyledonous species to transform individual plant cells and to achieve full, intact plants which can be regenerated from transformed plant cells and which express preselected polypeptides.

The introduced structural genes are expressed in the transformed plant cells and stably transmitted (somatically and sexually) to the next generation of cells produced. The vector should be capable of introducing, maintaining, and expressing a structural gene in plant cells. The structural gene is passed on to progeny by normal sexual transmission.

To confirm the presence of the structural gene (s) or "transgene(s)" in the regenerating plants, or seeds or progeny derived from the regenerated plant, a variety of assays can be performed. Such assays include Southern and Northern blotting; PCR; assays that detect the presence of a polypeptide product, e.g., by immunological means (ELISAs and Western blots) or by enzymatic function; plant part assays, such as leaf, seed or root assays; and also, by analyzing the phenotype of the whole regenerated plant.

Whereas DNA analysis techniques can be conducted using DNA isolated from any part of a plant, RNA will be expressed in the seed endosperm and hence it will be necessary to prepare RNA for analysis from these tissues.

PCR techniques can be used for detection and quantitation of RNA produced from introduced structural genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product.

Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the structural gene in question, they do not provide information as to whether the structural gene is being expressed. Expression may be evaluated by specifically identifying the polypeptide products of the introduced structural genes or evaluating the phenotypic changes brought about by their expression.

Assays for the production and identification of specific polypeptides may make use of physical-chemical, structural, functional, or other properties of the polypeptides. Unique physical-chemical or structural properties allow the polypeptides to be separated and identified by electrophoretic procedures, such as native or denaturing gel electrophoresis or isoelectric focusing, or by chromatographic techniques such as ion exchange or gel exclusion chromatography.

The unique structures of individual polypeptides offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques.

Additional techniques may be employed to absolutely confirm the identity of the product of interest such as evaluation by amino acid sequencing following purification. Although these are among the most commonly employed, other procedures may be additionally used.

Very frequently, the expression of a gene product is determined by evaluating the phenotypic results of its expression. These assays also may take many forms, including but not limited to, analyzing changes in the chemical composition, morphology, or physiological properties of the plant. In particular, the elevated preselected amino acid content due to the expression of structural genes encoding polypeptides can be detected by amino acid analysis.

Breeding techniques useful in the present invention are well known in the art.

The present invention will be further described by reference to the following detailed examples. It is understood, however, that there are many extensions, variations, and modifications on the basic theme of the present invention beyond that shown in the examples and description, which are within the spirit and scope of the present invention.

EXAMPLES

Example 1

Construction of the HT12 Gene and of Other Genes Encoding Polypeptides Having an Elevated Level of a Preselected Amino Acid.

As noted above, the sequence of the HT12 gene is based on the mRNA sequence of the native *Hordeum vulgare* alpha hordothionin gene (accession number X05901, Ponz et al. 1986 *Eur. J. Biochem.* 156:131–135) modified to introduce 12 lysine residues into the mature hordothionin peptide (See Rao et al. 1994 *Protein Engineering* 7(12):1485–1493, and WO 94/16078 published Jul. 21, 1994).

The alpha hordothionin cDNA comprising the entire alpha hordothionin coding sequence is isolated by rt-PCR of mRNA from developing barley seed. Primers are designed based upon the published alpha hordothionin sequence to amplify the gene and to introduce a NcoI site at the start (ATG) codon and a BamHI site after the stop codon of the thionin coding sequence to facilitate cloning.

Primers are designated as HTPCR1 Seq. 8 (5'-AGTATAAGTAAACACACCATCACACCCTTGAGGCCCT TGCTGGTGGCCATGG G-3') and HTPCR2 Seq. 9 (5'-CCTCACATCCCTTAGTGCCTAAGTTCGACGTCGG GCCCTCTAGTCGACGGATC CA-3'). These primers are used in a PCR reaction to amplify alpha hordothionin by conventional methods. The resulting PCR product is purified and subcloned into the BamHI/NcoI digested pBSKP vector (Stratagene, LaJolla, Calif.) and sequenced on both strands to confirm its identity. The clone is designated pBSKP-HT (seq. ID 1). Primers are designed for single stranded DNA site-directed mutagenesis to introduce 12 codons for lysine, based on the peptide structure of hordothionin 12 (Ref: Rao et al. 1994 *Protein Engineering* 7(12):1485–1493) and are designated

```
HT12mut1 Seq. 10 (5'-AGCGGAAAATGCCCGAAAGGCTTCCCCAAATTGGC-3'),

HT12mut2 Seq. 11 (5'-TGCGCAGGCGTCTGCAAGTGTAAGCTGACTAGTAGCGGAAAATGC-3'),

HT12mut3 Seq. 12 (5'-TACAACCTTTGCAAAGTCAAAGGCGCCAAGAAGCTTTGCGCAGGCGTCTG-3'),

HT12mut4 Seq. 13 (5'-GCAAGAGTTGCTGCAAGAGTACCCTGGGAAGGAAGTGCTACAACCTTTGC-3').
```

Sequence analysis is used to verify the desired sequence of the resulting plasmid, designated pBSKP-HT12 (seq. ID 2).

Similarly, genes encoding other derivatives of hordothionin, as described above, (See U.S. Pat. No. 5,990,389 issued Nov. 23, 1999; U.S. Pat. No. 5,885,801 issued Mar. 23, 1999; U.S. Pat. No. 5,885,802 issued Mar. 29, 1999; and U.S. Pat. No. 5,703,409 issued Dec. 30, 1997), the gene encoding enhanced soybean albumin (ESA) (See U.S. Pat. No. 5,850,016 issued Dec. 15, 1998), and genes encoding BHL and other derivatives of the barley chymotrypsin inhibitor (See WO 98/20133 published May 14, 1998) are constructed by site directed mutagenesis from pBSKP-HT, a subclone of the soybean 2S albumin 3 gene in the pBSKP vector (Stratagene, LaJolla, Calif.), and a subclone of the barley chymotrypsin inhibitor in the pBSKP vector, respectively.

Example 2

Construction of Vectors for Seed Preferred Expression of Polypeptides Having an Elevated Level of a Preselected Amino Acid.

A 442 bp DNA fragment containing the modified hordothionin gene encoding is HT12 is isolated from plasmid pBSKP-HT12 by NcoI/BamHI restriction digestion, gel purification and is ligated between the 27 kD gamma zein promoter and 27 kD gamma zein terminator of the NcoI/BamHI digested vector PHP3630. PHP 3630 is a subclone of the endosperm-preferred 27 kD gamma zein gene (Genbank accession number X58197) in the pBSKP vector (Stratagene), which is modified by site directed mutagenesis by insertion of a NcoI site at the start codon (ATG) of the 27 kD gamma zein coding sequence. The 27 kD gamma zein coding sequence is replaced with the HT12 coding sequence. The resulting expression vector containing the chimeric gene construct gz::HT12::gz, designated as PHP8001 (Seq. ID 3), is verified by extensive restriction digest analysis and DNA sequencing.

Similarly, the 442 bp DNA fragment containing the HT12 coding sequence is inserted between the globulin1 promoter and the globulin1 terminator of the embryo preferred corn globulin1 gene (Genbank accession number X59083), and between the waxy promoter and the waxy terminator of the endosperm-preferred waxy gene (Genbank accession number M24258). The globulin1 and waxy coding sequences, respectively, are replaced with the HT12 coding sequence. The resulting chimeric genes glb1::HT12::glb1, and wx::HT12::wx are designated as PHP 7999 (Seq. ID 4), and PHP 5025 (Seq. ID 5).

In a like manner, expression vectors containing genes encoding other derivatives of hordothionine (See Rao et al. 1994 *Protein Engineering* 7(12):1485–1493, and WO 94/16078 published Jul. 21, 1994, now U.S. Pat. No. 5,990, 389 issued Nov. 23, 1999), the gene encoding enhanced soybean albumin (ESA) (See U.S. Pat. No. 5,850,016), and genes encoding BHL and other derivatives of the barley chymotrypsin inhibitor (See WO 98/20133 published May 14, 1998) are constructed by insertion of the corresponding coding sequences between the promoter and terminator of the 27 kD gamma zein gene, the globulin1 gene and the waxy gene, respectively. Resulting chimeric genes are for example gz::ESA::gz and gz::BHL::gz, designated as PHP11260 (Seq. ID 6) and as PHP11427 (Seq. ID 7), respectively.

The resulting expression vectors are used in conjunction with the selectable marker expression cassettes PHP3528 (enhanced CAMV::Bar::PinII) for particle bombardment transformation of maize immature embryos.

Example 3

Preparation of Transgenic Plants

The general method of genetic transformation used to produce transgenic maize plants is mediated by bombardment of embryogenically responsive immature embryos with tungsten particles associated with DNA plasmids, said plasmids consisting of a selectable and an unselectable marker gene.

Preparation of Tissue

Immature embryos of "High Type II" are the target for particle bombardment-mediated transformation. This genotype is the $F_1$ of two purebred genetic lines, parent A and parent B, derived from A188 X B73. Both parents are selected for high competence of somatic embryogenesis. See Armstrong, et al., "Development and Availability of Germplasm with High Type II Culture Formation Response," *Maize Genetics Cooperation Newsletter*, Vol. 65, pp. 92 (1991); incorporated herein in its entirety by reference.

Ears from $F_1$ plants are selfed or sibbed, and embryos are aseptically dissected from developing caryopses when the scutellum first becomes opaque. The proper stage occurs about 9–13 days post-pollination, and most generally about 10 days post-pollination, and depends on growth conditions. The embryos are about 0.75 to 1.5 mm long. Ears are surface sterilized with 20–50% Clorox for 30 min, followed by 3 rinses with sterile distilled water.

Immature embryos are cultured, scutellum oriented upward, on embryogenic induction medium comprised of N6 basal salts (Chu, et al., "Establishment of an Efficient Medium for Anther Culture of Rice Through Comparative Experiments on the Nitrogen Sources," *Scientia Sinica*, (Peking), Vol. 18, pp. 659–668 (1975); incorporated herein in its entirety by reference; Eriksson vitamins (See Eriksson, T., "Studies on the Growth Requirements and Growth Measurements of *Haplopappus gracilis*," *Physiol. Plant*, Vol. 18, pp. 976–993 (1965); incorporated herein in its entirety by reference), 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l $AgNO_3$.

The medium is sterilized by autoclaving at 121° C. for 15 min and dispensed into 100×25 mm petri dishes. $AgNO_3$ is filter-sterilized and added to the medium after autoclaving. The tissues are cultured in complete darkness at 28° C. After about 3 to 7 days, generally about 4 days, the scutellum of the embryo has swelled to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per petri dish are located in the center of a petri dish in an area about 2 cm in diameter. The embryos are maintained on this medium for 3–16 hr, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 µl are deposited on macrocarriers and the ethanol allowed to evaporate. The macrocarrier is accelerated onto a stainless-steel stopping screen by the rupture of a polymer diaphragm (rupture disk). Rupture is effected by pressurized helium. Depending on the rupture disk breaking pressure, the velocity of particle-DNA acceleration may be varied. Rupture disk pressures of 200 to 1800 psi are commonly used, with those of 650 to 1100 psi being more preferred, and about 900 psi being most highly preferred. Rupture disk breaking pressures are additive so multiple disks may be used to effect a range of rupture pressures.

Preferably, the shelf containing the plate with embryos is 5.1 cm below the bottom of the macrocarrier platform (shelf #3), but may be located at other distances. To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A petri dish with the target embryos is placed into the vacuum chamber and located in the projected path of accelerated particles. A vacuum is created in the chamber, preferably about 28 inches Hg. After operation of the device, the vacuum is released and the petri dish is removed.

Bombarded embryos remain on the osmotically adjusted medium during bombardment, and preferably for two days subsequently, although the embryos may remain on this medium for 1 to 4 days. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite, 0.85 mg/l AgNO$_3$ and 3 mg/l bialaphos. Bialaphos is added filter-sterilized. The embryos are subcultured to fresh selection medium at 10 to 14 day intervals. After about 7 weeks, embryogenic tissue, putatively transgenic for both selectable and unselected marker genes, is seen to proliferate from about 7% of the bombarded embryos. Putative transgenic tissue is rescued, and that tissue derived from individual embryos is considered to be an event and is propagated independently on selection medium. Two cycles of clonal propagation is achieved by visual selection for the smallest contiguous fragments of organized embryogenic tissue.

For regeneration of transgenic plants, embryogenic tissue is subcultured to medium comprised of MS salts and vitamins (Murashige, T. and F. Skoog, "A revised medium for rapid growth and bio assays with tobacco tissue cultures"; *Physiologia Plantarum*; Vol. 15; pp. 473–497; 1962; incorporated herein in its entirety by reference), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm petri dishes and incubated in darkness at 28° C. until the development of well-formed, matured somatic embryos can be visualized. This requires about 14 days.

Well-formed somatic embryos are opaque and cream-colored, and are comprised of an identifiable scutellum and coleoptile. The embryos are individually subcultured to germination medium comprised of MS salts and vitamins, 100 mg/l myo-inositol, 40 gm/l sucrose and 1.5 gm/l Gelrite in 100×25 mm petri dishes and incubated under a 16 hr light: 8 hr dark photoperiod and 40 µEinsteinsm$^{-2}$sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hr light: 8 hr dark photoperiod and 40 µEinsteinsm$^{-2}$sec$^{-1}$ from cool-white fluorescent tubes.

After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

Preparation of Particles

Fifteen mg of tungsten particles (General Electric), 0.5 to 1.8 µm, preferably 1 to 1.8 µm, and most preferably 1 µm, are added to 2 ml of concentrated nitric acid. This suspension is sonicated at 0° C. for 20 min (Branson Sonifier Model 450, 40% output, constant duty cycle). Tungsten particles are pelleted by centrifugation at 10,000 rpm (Biofuge) for 1 min and the supernatant is removed. Two ml of sterile distilled water is added to the pellet and sonicate briefly to resuspend the particles. The suspension is pelleted, 1 ml of absolute ethanol is added to the pellet and sonicated briefly to resuspend the particles. Rinse, pellet, and resuspend the particles a further 2 times with sterile distilled water, and finally resuspend the particles in 2 ml of sterile distilled water. The particles are subdivided into 250 µl aliquots and stored frozen.

Preparation of Particle-Plasmid DNA Association

The stock of tungsten particles is sonicated briefly in a water bath sonicator (Branson Sonifier Model 450, 20% output, constant duty cycle) and 50 µl is transferred to a microfuge tube. Plasmid DNA is added to the particles for a final DNA amount of 0.1 to 10 µg in 10 µl total volume, and briefly sonicated. Preferably 1 µg total DNA is used. Specifically, 5 µl of PHP8001 (gz::HT12::gz) and 5 µl of PHP3528 (enhanced CAMV::Bar::PinII) at 0.1 µg/µl in TE buffer, are added to the particle suspension. Fifty µl of sterile aqueous 2.5 M CaCl$_2$ are added, and the mixture is briefly sonicated and vortexed. Twenty µl of sterile aqueous 0.1M spermidine are added and the mixture is briefly sonicated and vortexed. The mixture is incubated at room temperature for 20 min with intermittent brief sonication. The particle suspension is centrifuged, and the supernatant is removed. Two hundred fifty µl of absolute ethanol is added to the pellet and briefly sonicated. The suspension is pelleted, the supernatant is removed, and 60 µl of absolute ethanol is added. The suspension is sonicated briefly before loading the particle-DNA agglomeration onto macrocarriers.

Example 4

Analysis of Seed from Transgenic Plants for Recombinant Polypeptides Having an Elevated Level of a Preselected Amino Acid.

Preparation of Meals from Corn Seed

Pooled or individual dry seed harvested from transformed plants from the greenhouse or the field are prepared in one of the following ways:

A. Seed is imbibed in sterile water overnight (16–20 hr) at 4° C. The imbibed seed is dissected into embryo, endosperm and pericarp. The embryos and endosperm are separately frozen in liquid N$_2$, the pericarps are discarded. Frozen tissue is ground with a liquid N$_2$ chilled ceramic mortar and pestle to a fine meal. The meals are dried under vacuum and stored at –20° C. or –80° C.

B. Dry whole seed is ground to a fine meal with a ball mill (Klecko), or by hand with a ceramic mortar and pestle. For analysis of endosperm only, the embryos are removed with a drill and discarded. The remaining endosperm with pericarp is ground with a ball mill or a mortar and pestle.

ELISA Analysis

Rabbit polyclonal anti HT12 antisera are produced with synthetic HT12 (See Rao et al. supra) at Bethyl laboratories. An HT12 ELISA assay is developed and performed by the Analytical Biochemistry department of Pioneer Hi-Bred International, Inc., essentially as described by Harlow and Lane, Antibodies, A Laboratory Manual, Cold Springs Harbor Publication, New York (1988). Quantitative ELISA assays are first performed on pooled meals to identify positive events. Positive events are further analyzed by quantitative ELISA on individual kernels to determine the relative level of HT12 expression and transgene segregation ratio. Among 97 events tested, 59 show HT12 expression levels>1000 ppm. The highest events have HT12 expression levels at 2–5% of the total seed protein. Typical results for HT12 levels for whole kernels of wild type corn, for one event (TC2031) of corn transformed with the gz::HT12::gz chimeric gene, expressing HT12 in the endosperm, for one event (TC320) of corn transformed with the wx::HT12::wx chimeric gene, expressing HT12 in the endosperm, and for one event (TC2027) of corn transformed with the glb1::HT12::glb1chimeric gene, expressing HT12 in the embryo, are in Table 1.

Similarly, antisera are produced, ELISA assays are developed and assays of seed from transformed plants are performed for other derivatives of hordothionin (See Rao et al. 1994 *Protein Engineering* 7(12):1485–1493, and WO 94/16078 published Jul. 21, 1994, now U.S. Pat. No. 5,990,389 issued Nov. 23, 1999), for the enhanced soybean albumin (ESA) (See U.S. Pat. No. 5,850,016) and for BHL and other derivatives of the barley chymotrypsin inhibitor (See U.S. WO 98/20133 published May 14, 1998).

Polyacrylamide Gel and Immuno Blot Analysis

SDS extracts of meals, molecular weight markers, and a synthetic HT12 positive control (see Rao et al. supra) are separated on 16.5% or 8–22% polyacrylamide gradient Tris-Tricine gels (Schagger, H. and Von Jagow, G. 1987 *Anal. Biochem.*, 166:368). For immuno blot analysis, gels are transferred to PVDF membranes in 100 mM CAPS, pH 11; 10% methanol using a semidry blotter (Hoefer, San Francisco, Calif.). After transfer the membrane is blocked in BLOTTO (4% dry milk in Tris-buffered saline, pH 7.5) (Johnson, D. A., Gausch, J. W., Sportsman, J. R., and Elder, J. H. 1984, *Gene Anal. Techn.*, 1:3). The blots are incubated with rabbit anti-HT12 (same as used for ELISA) diluted 1:2000 to 1:7500 in BLOTTO 2 hr at room temperature (22° C.) or overnight at 4° C. Blots are washed 4–5× with BLOTTO, then incubated 1–2 hr with horseradish peroxidase-goat anti-rabbit IgG (Promega, Madison, Wis.) diluted 1:7500 to 1:15000 in BLOTTO. After secondary antibody, the blots are washed 3× with BLOTTO followed by 2 washes with Tris-buffered saline, pH 7.5. Blots are briefly incubated with enhanced chemiluminescence (ECL, Amersham, Arlington Heights, Ill.) substrate, and wrapped in plastic wrap. Reactive bands are visualized after exposure to x-ray film (Kodak Biomax MR) after short exposure times ranging from 5–120 sec.

HT12 transgenic seed shows a distinctive band not seen in wild type seed at the correct molecular weight and position as judged by the HT12 positive control standard and molecular weight markers. These results indicate that the expressed HT12 prepropeptide is being correctly processed like native HT in barley. Novel polypeptide bands co-migrating with the HT12 positive control are also observed in Coomassie stained polyacrylamide gels loaded with 10 mg total extracted protein indicating substantial expression and accumulation of HT12 protein in the seed.

Similarly, other derivatives of hordothionin, soybean albumin, the enhanced soybean albumin (ESA), BHL and other derivatives of the barley chymotrypsin inhibitor are detected by polyacrylamide gel and immuno blot analysis.

Amino Acid Composition Analysis

Meals from seed, endosperm or embryo that express a recombinant polypeptide having an elevated level of a preselected amino acid are sent to the University of Iowa Protein Structure Facility for amino acid composition analysis using standard protocols for digestion and analysis.

Typical results for the amino acid composition of whole kernels of wild type corn, for one event (TC2031) of corn transformed with the gz::HT12::gz chimeric gene, expressing HT12 in the endosperm, for one event (TC320) of corn transformed with the wx::HT12::wx chimeric gene, expressing HT12 in the endosperm, and for one event (TC2027) of corn transformed with the glb1::HT12::glb1 chimeric gene, expressing HT12 in the embryo, are in Table 1.

TABLE 1

HT12 ELISA analysis and amino acid composition of meal from whole kernels from wild type corn and from transformed corn expressing recombinant HT12.

| transgene | none | wx::HT12::wx | gz::HT12::gz | glb1::HT12::glb1 |
|---|---|---|---|---|
| event | wild-type | TC320 | TC2031 | TC2027 |
| ELISA | | | | |
| HT 12 | protein ppm | protein ppm | protein ppm | protein ppm |
| | 0.00 | 6200 | 8000 | 22600 |
| AA | | | | |
| | Meal % | Meal % | Meal % | Meal % |
| | n = 3 | n = 2 | n = 3 | n = 4 |
| Lys | 0.29 | 0.38 | 0.39 | 0.24 |
| Arg | 0.52 | 0.58 | 0.56 | 0.45 |
| Cys | 0.12 | 0.19 | 0.17 | 0.22 |

The results in Table 1 demonstrate corn expressing recombinant HT12 in the endosperm shows a significant increase of the preselected amino acid lysine.

TABLE 2

SEQUENCE INFORMATION

| SEQUENCE ID | PROMOTER | GENE |
|---|---|---|
| Seq. 1: pBSKP-HT | None | 3361–2947 |
| Seq. 2: pBSKP-HT12 | None | 3361–2947 |
| Seq. 3: PHP8001gz::HT12::gz expression vector | 676–2198 | 2199–2612 |
| Seq. 4: PHP7999 glb1::HT12::glb1 expression vector | 3271–1834 | 1834–1420 |
| Seq. 5: PHP5025 wx::HT::wx expression vector | 43–1342 | 1343–1757 |
| Seq. 6: PHP 11260 gz:ESA gz expression vector | 676–2198 | 2199–2675 |
| Seq. 7: PHP11427 gz::BHL::gz | 676–2198 | 2199–2450 |
| Seq. 8–13: artificial sequence primers | | |
| Seq. 14: Pea albumin, nucleotide sequence | | |
| Seq. 15: Pea albumin, protein sequence | | |
| Seq. 16: sulfur-rich 15KD maize protein, nucleotide sequence | | |
| Seq. 17: sulfur-rich 15KD maize protein, protein sequence | | |
| Seq. 18: methionine-rich 10KD maize protein, nucleotide sequence | | |
| Seq. 19: methionine-rich 10KD maize protein, protein sequence | | |
| Seq. 20: sulfur-rich rice prolamine, nucleotide sequence | | |
| Seq. 21: sulfur-rich rice prolamine, protein sequence | | |
| Seq. 22: wheat endosperm purothionin, protein sequence | | |

What is claimed is:

1. An expression cassette comprising a seed endosperm-preferred promoter operably linked to a polynucleotide encoding a barley alpha-hordothionin protein modified to contain one or both of about 7 mole % to about 40 mole % lysine or about 6 mole % to about 40 mole % of a sulfur-containing amino acid.

2. A method for increasing the level of one or both of lysine or sulfur-containing amino acids in a cereal plant seed, the method comprising:
   a) transforming a cereal plant cell with an expression cassette, and
   b) regenerating a transgenic cereal plant to produce a transgenic cereal plant seed,
   wherein the expression cassette comprises a seed endosperm-preferred promoter operably linked to a polynucleotide encoding a barley alpha-hordothionin protein modified to contain one or both of about 7 mole % to about 40 mole % lysine or about 6 mole % to about 40 mole % of a sulfur-containing amino acid and wherein the level of lysine or sulfur-containing amino acid is increased in the transgenic cereal plant seed compared to a corresponding non-transgenic cereal plant seed.

3. A transgenic cereal plant seed comprising a modified barley alpha-hordothionin polynucleotide operably linked to a seed endosperm-preferred promoter, wherein the polynucleotide encodes a barley alpha-hordothionin protein modified to contain one or both of about 7 mole % to about 40 mole % lysine or about 6 mole % to about 40 mole % of a sulfur-containing amino acid and wherein the transgenic cereal plant seed comprises an elevated level of lysine or sulfur-containing amino acid compared to a corresponding non-transgenic cereal plant seed.

4. A transgenic cereal plant comprising a modified barley alpha-hordothionin polynucleotide operably linked to a seed endosperm-preferred promoter, wherein the polynucleotide encodes a barley alpha-hordothionin protein modified to contain one or both of about 7 mole % to about 40 mole % lysine and/or about 6 mole % to about 40 mole % of a sulfur-containing amino acid and wherein transgenic seed of the transgenic cereal plant comprise an elevated level of lysine or sulfur-containing amino acid compared to a corresponding non-transgenic cereal plant seed.

5. A transgenic cereal plant cell comprising a barley alpha-hordothionin polynucleotide operably linked to a seed endosperm-preferred promoter, wherein the polynucleotide encodes a barley alpha-hordothionin protein modified to contain one or both of about 7 mole % to about 40 mole % lysine and/or about 6 mole % to about 40 mole % of a sulfur-containing amino acid and wherein transgenic seed resulting from the transgenic plant cell comprise one or both of an elevated level of lysine or sulfur-containing amino acid compared to a corresponding non-transgenic cereal plant seed.

6. A transgenic cereal plant seed produced by the method of claim 2.

7. The expression cassette according to claim 1 wherein the promoter is a gamma zein promoter or a waxy promoter.

8. A vector comprising the expression cassette of claim 1.

9. The transgenic cereal plant seed of claim 3 wherein the seed endosperm-preferred promoter is heterologous to the polynucleotide.

* * * * *